(12) United States Patent
Stewart

(10) Patent No.: US 7,875,207 B2
(45) Date of Patent: Jan. 25, 2011

(54) THERMALLY-RESPONSIVE MATERIALS AND DEVICES COMPRISING SUCH MATERIALS

(75) Inventor: Ray F. Stewart, Emerald Lake Hills, CA (US)

(73) Assignee: Bay Materials, LLC, Menlo Park, CA (US)

( * ) Notice: Subject to any disclaimer, the term of this patent is extended or adjusted under 35 U.S.C. 154(b) by 143 days.

(21) Appl. No.: 11/794,835

(22) PCT Filed: Dec. 23, 2005

(86) PCT No.: PCT/US2005/046956
§ 371 (c)(1),
(2), (4) Date: Nov. 4, 2008

(87) PCT Pub. No.: WO2006/073914
PCT Pub. Date: Jul. 13, 2006

(65) Prior Publication Data
US 2009/0108230 A1    Apr. 30, 2009

(51) Int. Cl.
*G01N 25/04* (2006.01)
(52) U.S. Cl. ............... 252/408.1; 116/207; 116/217
(58) Field of Classification Search ............ 252/408.1; 116/207, 217
See application file for complete search history.

(56) References Cited

U.S. PATENT DOCUMENTS

| | | |
|---|---|---|
| 4,006,780 A | 2/1977 | Zehr |
| 4,170,956 A | 10/1979 | Wear |
| 4,289,088 A | 9/1981 | Scibelli et al. |
| 4,896,728 A | 1/1990 | Wolff et al. |
| 5,495,865 A | 3/1996 | Wass et al. |
| 5,537,950 A | 7/1996 | Ou-Yang et al. |
| 5,622,137 A | 4/1997 | Lupton et al. |
| 5,919,404 A * | 7/1999 | Fujita et al. .............. 252/583 |
| 5,988,102 A | 11/1999 | Volk et al. |
| 6,176,197 B1 | 1/2001 | Thompson |
| 6,403,131 B1 | 6/2002 | Carmon |
| 6,672,370 B2 | 1/2004 | Searis et al. |
| 2005/0211153 A1 | 9/2005 | Ribi et al. |

FOREIGN PATENT DOCUMENTS

| | | | |
|---|---|---|---|
| GB | 2285130 | | 6/1995 |
| WO | WO 2006/073914 A3 * | | 7/2006 |

* cited by examiner

*Primary Examiner*—John R Hardee
(74) *Attorney, Agent, or Firm*—Judy Mohr; King & Spalding LLP

(57) ABSTRACT

Devices are described that include a component comprised of a material having a structure of $R^1$—C(O)—NX—$R^2$, wherein each of $R^1$ and $R^2$ is independently a saturated alkyl having between 7-22 carbon atoms or an aryl, X is H or C(O)—Y, Y together with $R^1$ forms a ring. The material is characterized by a single, sharp melting point, thus making it suitable for use, for example, in thermomechanical actuating devices or in temperature-indicating devices. Also described are compositions comprising two or more materials each having a structure of $R_n^1$—C(O)—NH—$R^2$ wherein, n is an identifying integer corresponding to a material in the composition; wherein for each material n in the composition, $R_n^1$ and $R_n^2$ are a saturated alkyl having between 7-22 carbon atoms, wherein for each material n $R_n^1$ and $R_n^2$ differ by one carbon atom, and wherein the number of carbon atoms in $R_n^2$ of each material n differs by four or less.

15 Claims, 19 Drawing Sheets

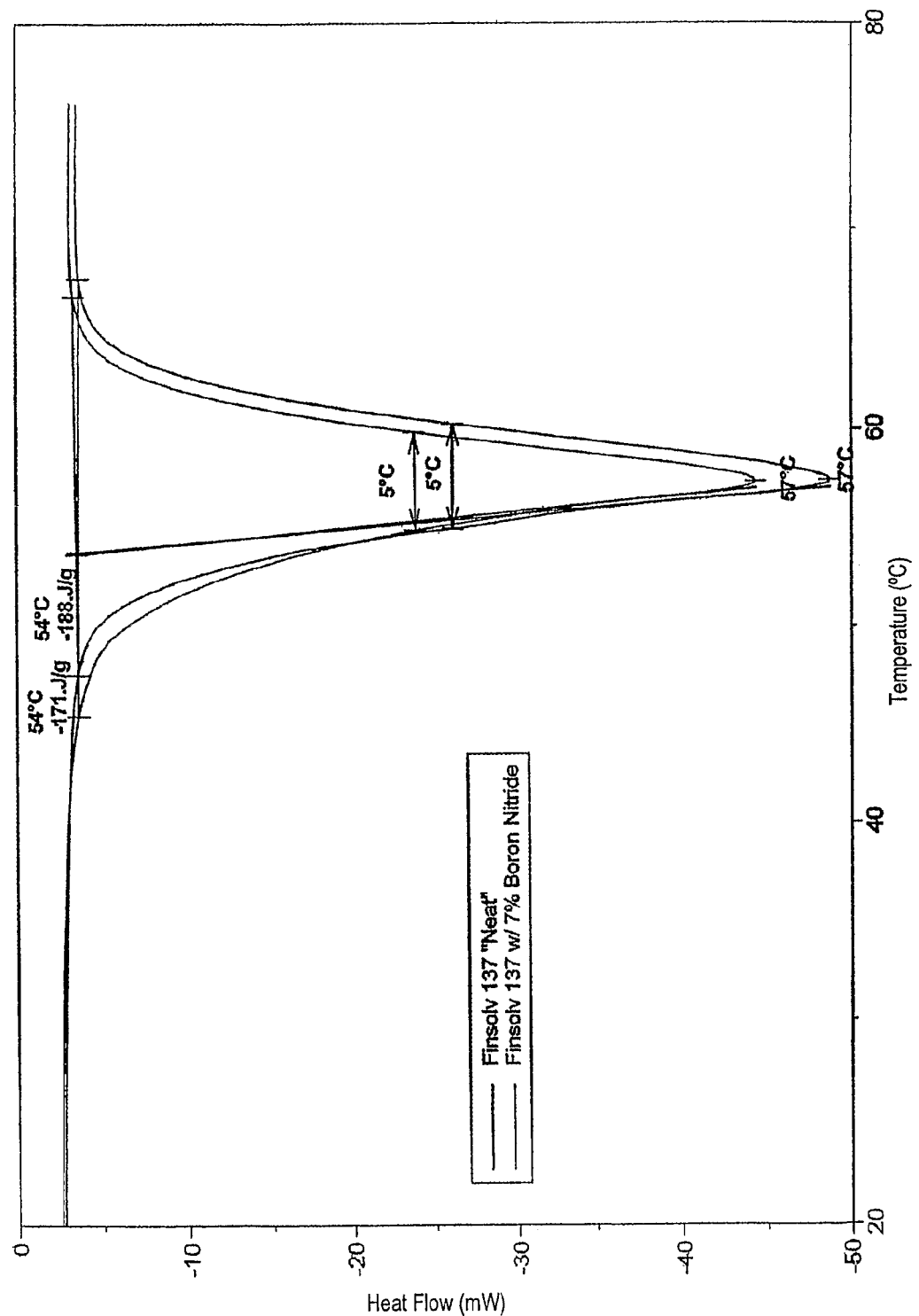

THERMALLY-RESPONSIVE MATERIALS AND DEVICES COMPRISING SUCH MATERIALS

This application is a 35 USC §371 application of International Application No. PCT/US2005/046956 filed Dec. 23, 2005, designating the United States, which claims priority to U.S. Application No. 60/641,989 filed Jan. 7, 2005, now abandoned, and to U.S. Application No. 60/671,929 filed Apr. 15, 2005, now abandoned, all of which are hereby incorporated by reference in their entirety.

TECHNICAL FIELD

The present subject matter relates to material compositions that undergo a thermal transition over a narrow temperature range and to devices prepared from the compositions.

BACKGROUND

A variety of devices in a wide range of industries include one or more component parts prepared from a material that undergoes a phase change at a temperature of interest. As the material undergoes the phase change, the component part typically expands or contracts, inducing a reaction, such as movement of an adjacent component part. For example, mechanical actuators are known where a material, typically a metal alloy, a polymer, or a wax, in the actuator expands or contracts to effect movement of a part in the actuator (U.S. Pat. Nos. 5,025,627; 5,177,969). Temperature relief valves having a thermal trigger composed of a eutectic material are known (U.S. Pat. No. 5,495,865). Fire sprinklers and fire extinguishes having a component part that responds to temperature increases are known (U.S. Pat. Nos. 4,896,728; 4,006,780). Temperature indicating devices for use in the medical industry and in the food industry are also known, where a component in the temperature-indicating device is composed of a material that undergoes a phase change at a selected temperature (U.S. Pat. Nos. 4,289,088; 4,170,956; 5,537,950; 5,988,102; 6,403,131). In these devices, a spring loaded indicator is held in place by a small quantity of meltable material, generally a eutectic metal alloy or an organic compound.

These and other devices require materials, preferably organic compounds, that exhibit very sharp melting points in the range of 50 to 100° C. There are few eutectic metal alloys that have a melting temperature in this temperature range of interest. Of the eutectic metal alloys available, for example lead/cadmium mixtures, toxicity of the material can be an issue for actuators used the medical or food industries. Moreover, low melting eutectic alloys are costly. Similarly, there are few organic compounds that have melting points in this temperature range of interest, and of those that do have the requisite melting point, often a physical or chemical property renders the compound undesirable for use in an actuator device.

Another problem with existing metallic and organic compounds is that it is not possible to vary the melting point and maintain abrupt melting behavior. For example, if the composition of an eutectic alloy is changed slightly, the melting point will either not change, broaden unacceptably, or give multiple melting points. Likewise, if a pure organic compound having a melting point at for example 85° C. is mixed with another compound the melting point of the mixture will invariably be lower and occur over a broader range. Moreover, while melting is a thermodynamic property, the behavior of a mechanical device, such as a food temperature indicator or a fire sprinkler, will be sensitive to the mechanical properties of the materials used. Many organic compounds having what appear to be sharp melting points, in fact do not provide the necessary mechanical properties for use in a thermo-mechanical device.

It would be very desirable to have a series of organic materials where the melting properties could be smoothly varied up or down while maintaining the necessary mechanical properties for use in a thermo-mechanical device. There remains a need in the art for such materials, and more specifically materials that have the following general properties: (i) a melting point between about 50 and about 100° C.; (ii) non toxic to humans; (iii) a low vapor pressure at 120° C.; (iv) stability at elevated temperature and moisture; (v) no odor; (vi) rapid rate of crystallization; (vii) low cost; (viii) readily produced in high purity; and (ix) sharp melting point and abrupt change in viscosity with temperature change.

SUMMARY

In one aspect, a device comprising a material having a structure of $R^1$—C(O)—NX—$R^2$, wherein each of $R^1$ and $R^2$ is independently a saturated alkyl having between 7-22 carbon atoms or an aryl, X is H or C(O)—Y, Y together with $R^1$ forms a ring is describe. The device has a temperature range over which a trigger temperature occurs of less than about 2° C.

In one embodiment the material has the structure $R^1$—C(O)—NH—$R^2$, where the number of carbon atoms in $R^1$ and $R^2$ differs by an absolute value of four or less.

In another embodiment, $R^1$ is a saturated alkyl having between 7-21 carbon atoms and $R^2$ is a saturated alkyl having between 8-22 carbon atoms, wherein the number of carbon atoms in $R^2$ differs from the number of carbon atoms in $R^1$ by an absolute value of one, two, or three.

Specific examples of preferred materials include where $R^1$ is $CH_3(CH_2)_{10}$ and $R^2$ is $CH_3(CH_2)_{11}$; where $R^1$ is $CH_3(CH_2)_8$ and $R^2$ is $CH_3(CH_2)_{11}$; where $R^1$ is $CH_3(CH_2)_{16}$ and $R^2$ is $CH_3(CH_2)_{17}$; wherein $R^1$ is $CH_3(CH_2)_{14}$ and $R^2$ is $CH_3(CH_2)_{15}$; and where $R^1$ is $CH_3(CH_2)_{20}$ and $R^2$ is $CH_3(CH_2)_{17}$.

In another embodiment, the device comprises a second material having a structure of $R_2^1$—C(O)—NH—$R_2^2$, wherein each of $R_2^1$ and $R_2^2$ is independently a saturated alkyl having between 7-22 carbon atoms, and wherein the number of carbon atoms in $R_2^2$ differs from the number of carbon atoms in $R^2$ by an absolute value of four or less.

In one embodiment, wherein each of $R^1$ and $R_2^1$ are independently a saturated alkyl having between 9-19 carbon atoms, and each of $R^2$ and $R_2^2$ are independently a saturated alkyl having between 10-20 carbon atoms, wherein the number of carbon atoms in $R^1$ or $R^2$ is greater than the number of carbon atoms in $R_2^1$ or $R_2^2$ by one, two, three, or four. In an alternative embodiment, $R^1$ and $R_2^1$ are independently a saturated alkyl having between 9-19 carbon atoms, and each of $R^2$ and $R_2^2$ are independently a saturated alkyl having between 10-20 carbon atoms, wherein the number of carbon atoms in $R^2$ is greater than the number of carbon atoms in $R_2^2$ by two or four.

Specific examples of blends include wherein $R^1$ is $CH_3(CH_2)_{10}$ and $R^2$ is $CH_3(CH_2)_{11}$ and wherein $R_2^1$ is $CH_3(CH_2)_{14}$ and $R_2^2$ is $CH_3(CH_2)_{15}$. Another example is where $R^1$ is $CH_3(CH_2)_{16}$ and $R^2$ is $CH_3(CH_2)_{17}$ and wherein $R_2^1$ is $CH_3(CH_2)_{12}$ and $R_2^2$ is $CH_3(CH_2)_{13}$. Another example is where $R^1$ is $CH_3(CH_2)_{14}$ and $R^2$ is $CH_3(CH_2)_{15}$ and wherein $R_2^1$ is $CH_3(CH_2)_{12}$ and $R_2^2$ is $CH_3(CH_2)_{13}$. Yet another example is where $R^1$ is $CH_3(CH_2)_{16}$ and $R^2$ is $CH_3(CH_2)_{17}$ and wherein $R_2^1$ is $CH_3(CH_2)_{14}$ and $R_2^2$ is $CH_3(CH_2)_{15}$. Still another example is where $R^1$ is $CH_3(CH_2)_{16}$ and $R^2$ is $CH_3(CH_2)_{17}$ and wherein $R_2{}^1$ is $CH_3(CH_2)_{20}$ and $R_2{}^2$ is $CH_3(CH_2)_{21}$.

In another embodiment, the material has a structure of $R^1$—C(O)—NH—$R^2$, wherein $R^1$ is aryl and $R^2$ is a saturated alkyl having between 8-22 carbon atoms. An exemplary material is where $R^2$ is $CH_3(CH_2)_{15}$ or $CH_3(CH_2)_{17}$.

In another embodiment, the material has a structure of $R_2{}^1$—C(O)—NH—$R_2{}^2$, where $R_2{}^1$ is aryl and $R_2{}^2$ is a saturated alkyl having between 8-22 carbon atoms, wherein the number of carbon atoms in $R_2{}^2$ differs from the number of carbon atoms in $R^2$ by an absolute value of four or less, excluding zero.

For example, in this embodiment, $R^2$ can be a saturated alkyl having between 14-20 carbon atoms and $R_2{}^2$ can be a saturated alkyl having between 14-20 carbon atoms, wherein the number of carbon atoms in $R_2{}^2$ differs from the number of carbon atoms in $R^2$ by an absolute value of one, two, or three. One specific example is where $R^2$ is $CH_3(CH_2)_{15}$ and $R_2{}^2$ is $CH_3(CH_2)_{17}$.

In another embodiment, the material has a structure of $R^1$—C(O)—NH—$R^2$ wherein $R^1$ is a saturated alkyl having between 8-22 carbon atoms and $R^2$ is aryl. Specific examples include where $R^1$ is selected from the group consisting of $CH_3(CH_2)_{10}$, $CH_3(CH_2)_{12}$, and $CH_3(CH_2)_{14}$.

In yet another embodiment, the device comprises a second material having a structure of $R_2{}^1$—C(O)—NH—$R_2{}^2$, wherein $R_2{}^1$ is a saturated alkyl having between 8-22 carbon atoms and $R_2{}^2$ is aryl, wherein the number of carbon atoms in $R_2{}^1$ differs from the number of carbon atoms in $R^1$ by an absolute value of four or less, excluding zero.

In another embodiment, $R^1$ is a saturated alkyl having between 14-20 carbon atoms and $R_2{}^1$ is a saturated alkyl having between 14-20 carbon atoms, wherein the number of carbon atoms in $R_2{}^1$ differs from the number of carbon atoms in $R^1$ by an absolute value of one, two, or three.

A specific example is where $R^1$ is $CH_3(CH_2)_{12}$ and $R_2{}^1$ is $CH_3(CH_2)_{10}$.

Generally, the device comprised of a material as described above can have an activation or trigger temperature of between about 70-100° C., in one embodiment.

In another embodiment, the material further comprises a filler, which can, for example, be present in an amount between 5-35 weight percent. The filler can be, but need not be, thermally conductive. Exemplary fillers include, but are not limited to, mica, calcium carbonate, boron nitride, and a benzoate salt.

In another embodiment, the material further comprises a nucleating agent. When present, it can be added in an amount between 0.01-1 weight percent. Exemplary agents include, but are not limited to boron nitride, calcium carbonate, wollastonite, zinc oxide, magnesium oxide, and alumina.

In another aspect, a composition comprising two or more materials each having a structure of $R_n{}^1$—C(O)—NH—$R_n{}^2$, wherein, n is an identifying integer corresponding to a material in the composition is described. For each material n in the composition, $R_n{}^1$ and $R_n{}^2$ are a saturated alkyl having between 7-22 carbon atoms, wherein for each material n $R_n{}^1$ and $R_n{}^2$ differ by one carbon atom, and wherein the number of carbon atoms in $R_n{}^2$ of each material n differs by four or less.

In yet another aspect, a device comprised of any of the materials described above is described.

In yet another aspect, the use of any of the materials described above as a temperature indicating means or in a temperature indicating device is provided.

In still another aspect, a composition comprised of A and B is described, wherein (i) A and B are compounds dependently selected from the group consisting of linear alkyl amides, benzamides, and anilides, (ii) A and B individually differ in carbon number by an absolute value of from 2 to 4, (iii) A and B individually have a purity of greater than 95 wt %, (iv) A and B are present in a ratio of from 90:10 to 10:90, and (v) the composition contains less than 0.5 wt % of collectively alkyl amine, alkyl nitrile, and amic acid.

In addition to the exemplary aspects and embodiments described above, further aspects and embodiments will become apparent by reference to the drawings and by study of the following descriptions.

BRIEF DESCRIPTION OF THE DRAWINGS

FIGS. 6A-6B show DSC heating (FIG. 6A) and cooling (FIG. 6B) scans for behenyl benzoate neat and with addition of boron nitride;

DETAILED DESCRIPTION

I. Definitions

Figure 1A:
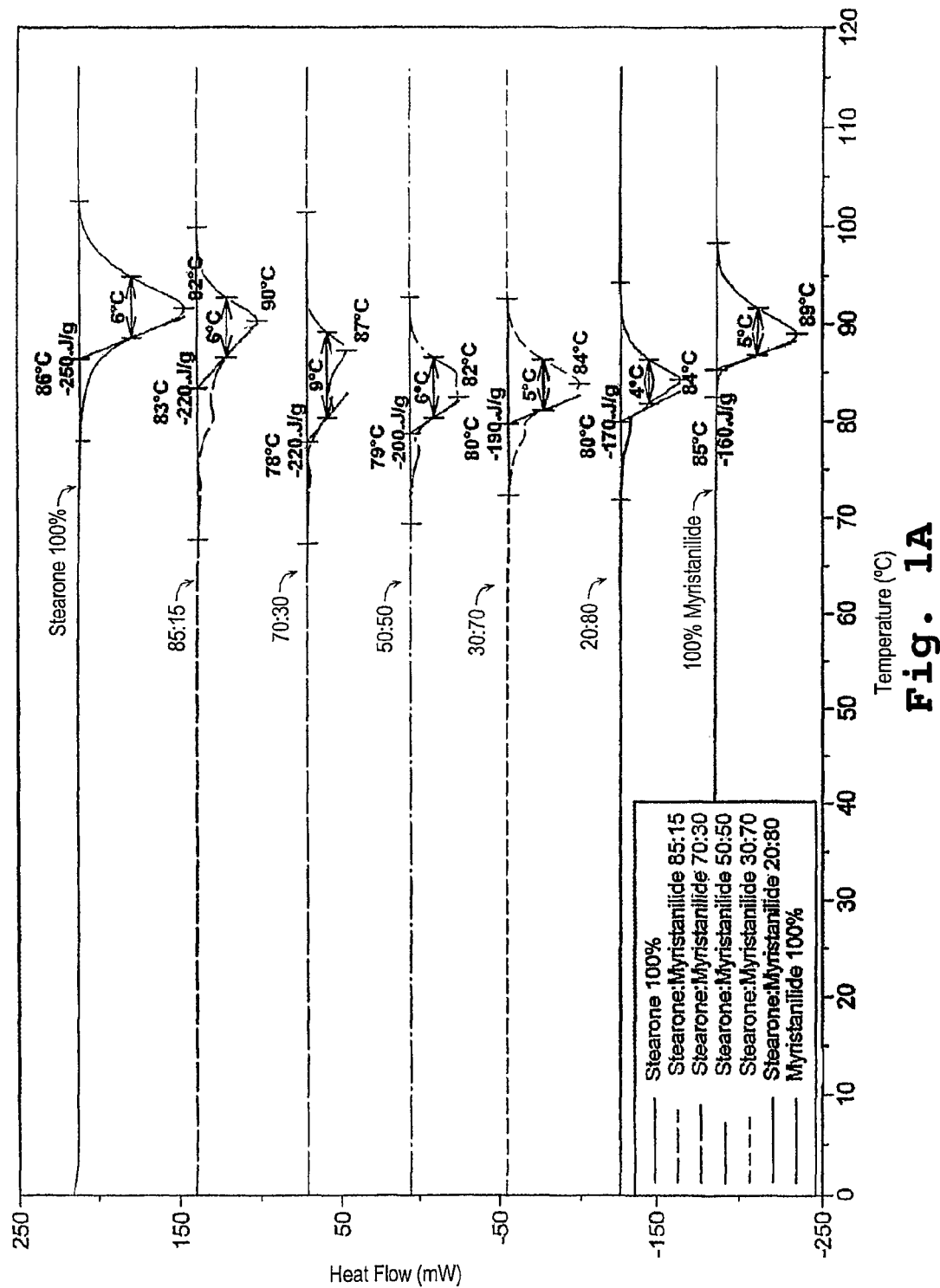
FIGS. 1A-1B are differential scanning calorimetry (DSC) scans generated upon heating (FIG. 1A) and cooling (FIG. 1B) a comparative, prior art composition comprised of stearone and myristanilide at the indicated weight ratios.

"Trigger temperature" intends a temperature, or range of temperatures, at which a device signals attainment of its predetermined temperature. The trigger temperature is easily determined, for example, by suspending the device in an appropriate liquid bath so that the tip and most of the body of the device (but not the top), is submerged. The temperature of the bath is controlled so that it cycles within a ±0.55° C. temperature range. The bath is held at each temperature for two minutes after which the temperature is raised in 0.55° C. increments to the next temperature. The temperature at which the device "fires" or is triggered is recorded. Typically, a trigger temperature for a given device is determined based on an average of trigger temperatures of at least three, preferably five, devices.

"Melting temperature" or "melting point" refers to the onset temperature at which a material begins to melt. At the melting temperature, the material becomes ductile, malleable, or deformable; the term does not imply that the whole of a material has melted.

"Melting range" refers to the temperature interval over which all of a material melts. Melting ranges are readily determined, for example using differential scanning calorimetry.

"Yield temperature" refers to the temperature at which a material yields or gives in response to a stress. The yield temperature is typically near the melting temperature, however the yield temperature can differ from the melting temperature for certain materials.

"Thermomechanical analysis" (TMA) and "Dynamic Mechanical Thermal Analysis" (DMA or DMTA) are techniques by which the dimensional or rheological property changes of a sample are monitored as a function of temperature or time, while the sample may be subjected to an additional mechanical load. Testing methods for TMA are typically done in accord with one of the following tests: DIN 51045, ASTM E 831, ASTM D 696, ASTM D 3386. TMA performance is a predictor for a material's trigger temperature and mechanical performance in a thermo-mechanical device, such as an actuator.

II. Compositions

In one aspect, compositions that undergo a primary phase change in response to a temperature change, the phase change occurring over a narrow temperature range of at most 6° C., preferably of at most 4° C., as measured by, for example, differential scanning calorimetry (DSC, at a scan rate of about 10° C.) or thermal mechanical analysis (TMA) are provided. More specifically, the phase change when measured by DSC at a scan rate of around 5° C. or 10° C. will have a peak width at ⅓ height of about 4-6° C. Moreover, the compositions when incorporated into a device exhibit mechanical properties at an operating temperature of interest that provide acceptable device performance. Typically the operating temperature is one that approaches the temperature at which the composition undergoes its phase change.

As noted above, materials that undergo phase changes, such as a solid-liquid melting point, are known in the art. However, not all materials that undergo a phase change are suitable for use in thermo-mechanical devices, as illustrated with the materials prepared from mixtures of stearone and stearyl stearamide (Comparative Example 1) and from mixtures of stearone and myristanalide (Comparative Example 2). These comparative examples illustrate the difficulties in preparing a composition with a desired melting point that occurs over a definite, narrow range. For example, suppose a material with a melting point of 90° C. is desired for use in an actuator. A skilled person can observe that stearone, with a melting point of 92° C., and myristanalide, with a melting point of 89° C., could potentially be mixed to arrive at a composition that melts at 90° C. Comparative Example 2 shows that an 85:15 stearone:myristanalide mixture provides a composition with a melting point of 90° C. (see FIG. 1A and Table 2 in Comparative Example 2). However, the melting point of 90° C. is preceded by an earlier transition at about 80° C. (a double peak in the DSC scan) and occurs over a wide temperature range of 10° C.

Accordingly, compositions that provide a desired melting point over a narrow 4-6° C. temperature range and that exhibit mechanical properties that are suitable for use in thermo-mechanical devices are desired, and provided by the compositions described herein.

Studies were performed using materials prepared from compounds of the form $R^1$—C(O)—NX—$R^2$, where each of $R^1$ and $R^2$ is independently a saturated alkyl having between 7-22 carbon atoms or an aryl, X is H or C(O)—Y, Y together with $R^1$ forms a ring. These studies will now be described with reference to Examples 1-3.

Example 1 describes a first series of studies conducted on aliphatic amides and blends of aliphatic amides. Aliphatic amides are of the form $R^1$—C(O)—NH—$R^2$, where $R^1$ is a saturated alkyl having between 7-21 carbon atoms and $R^2$ is a saturated alkyl having between 8-22 carbon atoms. Aliphatic amides were prepared by combining equal molar amounts of a selected aliphatic amine and a selected aliphatic carboxylic acid, as detailed in Example 1A. Seven different materials were prepared and their melting transitions evaluated using DSC. The results are shown in Table 3A.

TABLE 3A

| Designation | Chemical Name | *$R^1$ | *$R^2$ | Melting Point (° C.) | Melting Range (° C.) | Comment re DSC Peak Shape |
|---|---|---|---|---|---|---|
| N-12-12 | n-dodecyl dodecamide | $CH_3(CH_2)_{10}$ | $CH_3(CH_2)_{11}$ | 80 | 4 | Symmetrical |
| N-18-8 | n-octadecyl octamide | $CH_3(CH_2)_6$ | $CH_3(CH_2)_{17}$ | 82 | 5 | Symmetrical |
| N-18-10 | n-octadecyl decamide | $CH_3(CH_2)_8$ | $CH_3(CH_2)_{17}$ | 85 | 5 | Symmetrical |
| N-18-12 | n-octadecyl dodecamide | $CH_3(CH_2)_{10}$ | $CH_3(CH_2)_{17}$ | 88 | 4 | Symmetrical |
| N-12-10 | n-dodecyl decamide | $CH_3(CH_2)_8$ | $CH_3(CH_2)_{11}$ | 67 | 6 | Symmetrical |
| N-18-18 | n-octdecyl octadecamide | $CH_3(CH_2)_{16}$ | $CH_3(CH_2)_{17}$ | 98 | 5 | Symmetrical |
| N-16-16 | n-hexadecyl hexadecamide | $CH_3(CH_2)_{14}$ | $CH_3(CH_2)_{15}$ | 95 | 6 | Symmetrical |

*$R^1$—C(O)—NH—$R^2$

The materials were then tested to determine if they exhibited suitable mechanical properties for use in a device. The trigger temperatures of the materials when incorporated into a device were determined according to the method described above and in U.S. Pat. No. 5,537,950, incorporated by reference herein. The results are shown in Table 3B.

TABLE 3B

| Compound[1] | Trigger Temperature (° C.) | Trigger Range (° C.) |
|---|---|---|
| N-12-12 | 76 | 2 |
| N-12-10 | 58 | 2 |

TABLE 3B-continued

| Compound[1] | Trigger Temperature (° C.) | Trigger Range (° C.) |
|---|---|---|
| N-18-12 | 85 | 6 |
| N-18-8 | 73[2] | 8[2] |
| N-18-10 | 81 | 7[2] |

[1]see Table 3A for composition
[2]estimated using DSC.

The data in Table 3B demonstrates that it is not sufficient for the composition to simply have a sharp melting point to exhibit the necessary mechanical properties for use in a temperature responsive device. For example, the materials designated as N-18-12 and N-18-8 have sharp melting points, but give poor triggering behavior as evidenced by the wide trigger ranges of 6° C. and 8° C., respectively. This data also suggests that it may be desirable that the aliphatic amide be relatively symmetrical in structure. That is, aliphatic amides are preferably of the form $R^1$—C(O)—NH—$R^2$ where the absolute value of $R^2$–$R^1$ is less than about four, i.e., is 0, 1, 2, or 3. That is, the number of carbon atoms in $R^2$ differs from than the number of carbon atoms in $R^1$ by an absolute value of zero, one, two, or three.

In another study, materials of the form $R^1$—C(O)—NX—$R^2$, where each of $R^1$ and $R^2$ is independently a saturated alkyl having between 7-22 carbon atoms or an aryl, X is C(O)—Y, Y together with $R^1$ forms a ring, were prepared. Specifically, 1,4-bis(oxytetradecyl)piperazine and 1,4-bis(oxyhexadecyl)piperazine were synthesized and analyzed by DSC. Table 4 shows the DSC results.

TABLE 4

| Designation | Chemical Structure | Melting Point (° C.) | Melting Range (° C.) | Comment re DSC Peak Shape |
|---|---|---|---|---|
| N-14-14-P | 1,4-bis(oxytetra-decyl)piperazine | 69 | 6 | Symmetrical |
| N-16-16-P | 1,4-bis(oxyhexa-decyl)piperazine | 83 | 5 | Symmetrical |

The material designated as N-16-16-P was tested to determine if it exhibited suitable mechanical properties for use in a device. The trigger temperature of the material when incorporated into a device was determined according to the method described above and in U.S. Pat. No. 5,537,950. The material had a trigger temperature of 80° C. which occurred over a temperature range of 1.7° C.

Compositions comprised of a first material of the form $R^1$—C(O)—NH—$R^2$ (where $R^1$ and $R^2$ are as defined above) and a second material of the form $R_2^1$—C(O)—NH—$R_2^2$, where each of $R_2^1$ and $R_2^2$ is independently a saturated alkyl having between 7-22 carbon atoms are provided. The number of carbon atoms in $R_2^2$ differs from the number of carbon atoms in $R^2$ by an absolute value of four or less, i.e., by 3, 2, 1, or 0. In support of this, a study was conducted where a series of blends of symmetrical and unsymmetrical aliphatic amides were prepared, as described in Example 1B. The materials were characterized by DSC and the results are shown in Table 5 and in FIGS. 2A-2E.

TABLE 5

| Composition Identification No.[1] | First Compound Designation (wt %) | Second Compound Designation (wt %) | Melting Point (° C.) | Melting Range (° C.) | Comment re. DSC scan |
|---|---|---|---|---|---|
| 1 | N-18-18 (60) | N-18-12 (40) | 88 | 12 | Two peaks |
| 2 | N-18-18 (5) | N-18-12 (95) | 83 | 12 | Very Broad |
| 3 | N-18-18 (8) | N-12-12 (92) | 72, 77 | 9 | Large shoulder |
| 4 | N-18-18 (10) | N-18-8 (90) | 80 | 9 | Broad onset |
| 5 | N-16-16 (0) | N-12-12 (100) | 80 | 4 | Symmetrical |
| 6 | N-16-16 (30) | N-12-12 (70) | 74 | 6 | Symmetrical |
| 7 | N-16-16 (50) | N-12-12 (50) | 77 | 7 | Small onset shoulder |
| 8 | N-16-16 (70) | N-12-12 (30) | 76, 85 | 15 | Two peaks |
| 9 | N-16-16 (100) | N-12-12 (0) | 95 | 6 | Symmetrical |
| 10 | N-16-16-P (60) | N-14-14-P (40) | 64, 72 | 8,15 | Two Peaks |

[1]Refer to Example 1.A2 for additional details on blend compositions.

Figure 2A:
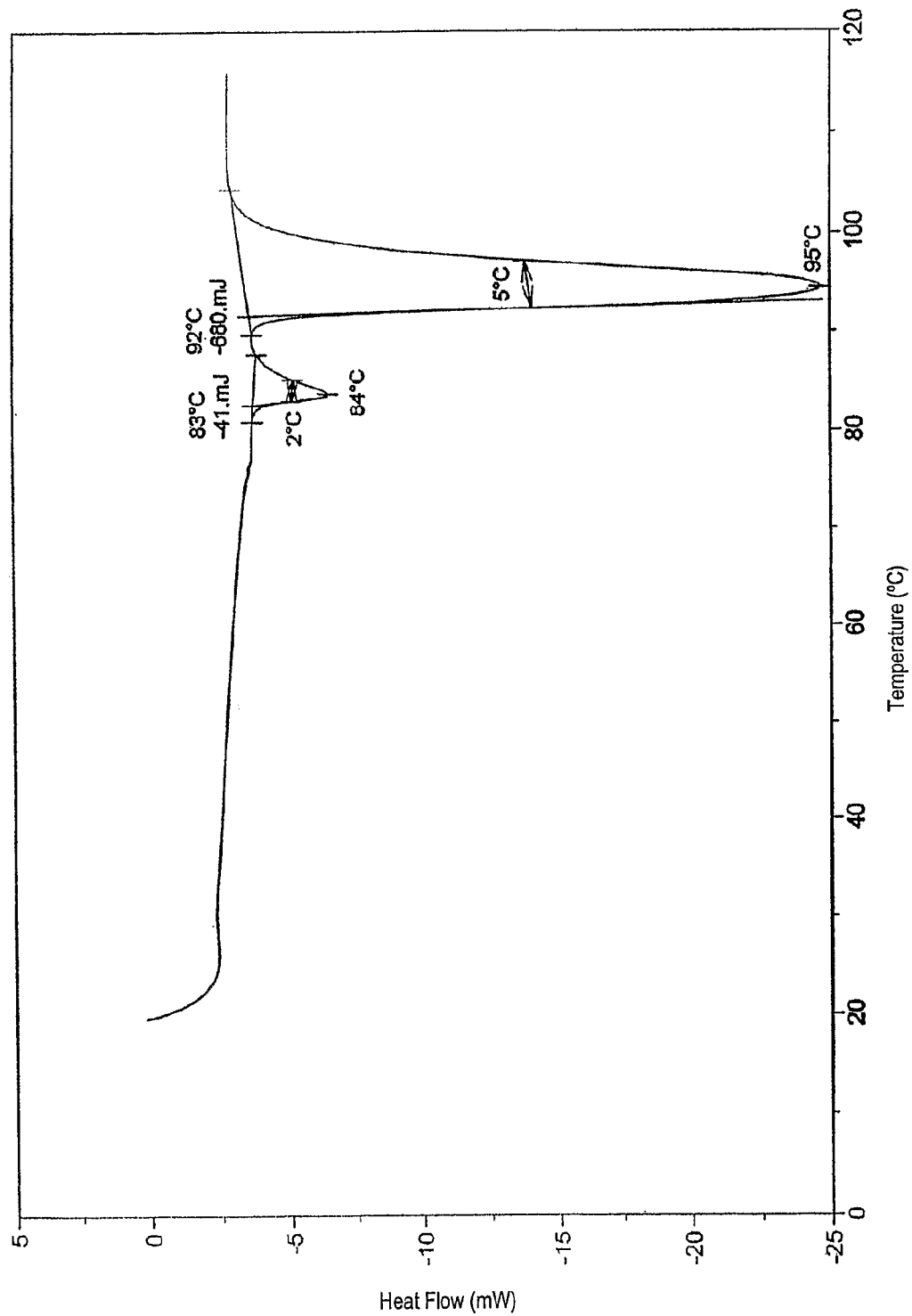
FIGS. 2A-2E are DSC scans of n-hexadecyl hexadecamide (FIG. 2A) and of lauryl lauramide (FIG. 2E) and of blends comprised of n-hexadecyl hexadecamide/lauryl lauramide in weight ratios of 70:30 (FIG. 2B), 50:50 (FIG. 2C), and 30:70 (FIG. 2D)
Figure 2B:
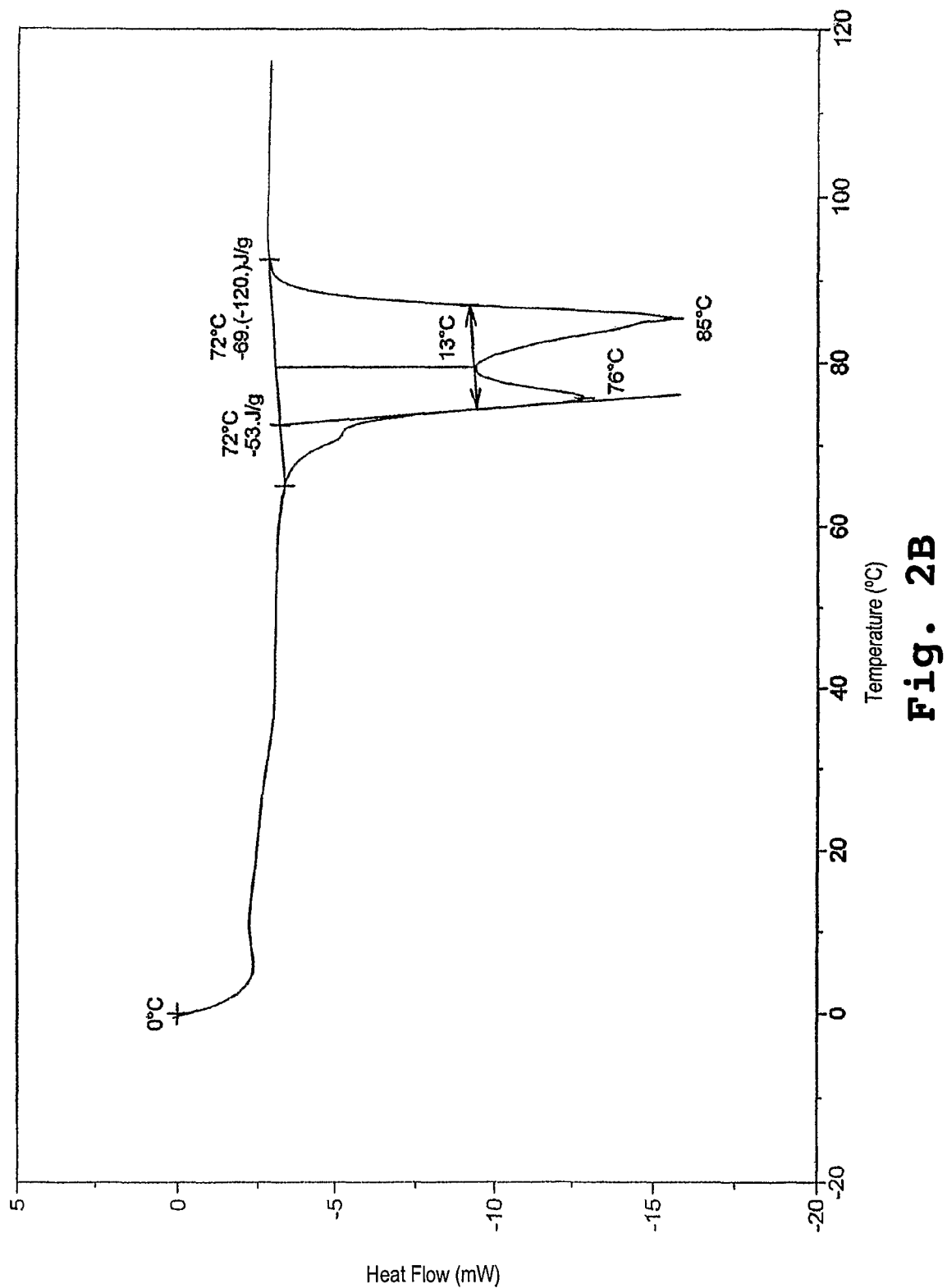

As can be seen from the data, mixing two or more compounds, even when they are structurally similar results is a significant broadening of the melting range in most instances and frequently results in multiple peaks. For example, blend no. 1, comprised of 60:40 weight percent mixture of n-octadecyl octadecamide/n-octadecyl dodecamide exhibited two melting peaks in the DSC scan, with a melting range of 12° C. The two components, n-octadecyl octadecamide and n-octadecyl dodecamide are structurally similar, differing only by six carbon atoms in the carbon chain attached to the carboxyl moiety in the amide. This is further illustrated by the DSC scans shown in FIGS. 2A-2E, which correspond to blends of n-hexadecyl hexadecamide and of n-lauryl lauramide (also known as n-dodecyl dodecamide). FIG. 2A shows the DSC scan for 100% n-hexadecyl hexadecamide, which exhibits a melting point of 95° C. and a melting range of 5° C. The minor peak at 84° C. is an unknown component, possibly an amine acid salt or other impurity present in a trace amount. FIG. 2E shows the melting point of 100% n-lauryl lauramide at 83° C., with a range of 7° C. Blends comprised of n-hexadecyl hexadecamide and n-lauryl lauramide in weight ratios of 70:30 (FIG. 2B), 50:50 (FIG. 2C), and 30:70 (FIG. 2D) are shown in the indicated figures. The 70:30 blend exhibits a double peak, with melting points at 76° C. and at 85° C. for the two components. The double peak is evidence that the two components are unable to pack into the same crystalline unit, even though the components differ only by an absolute value four carbon atoms in their aliphatic chains (i.e., 16 carbon atoms in each carbon tail, $R^1$, $R^2$, of the hexadecyl hexadecamine component and 12 carbon atoms in each carbon tail, $R_2{}^1$, $R_2{}^2$, of the lauryl lauramide component).

Figure 2C:
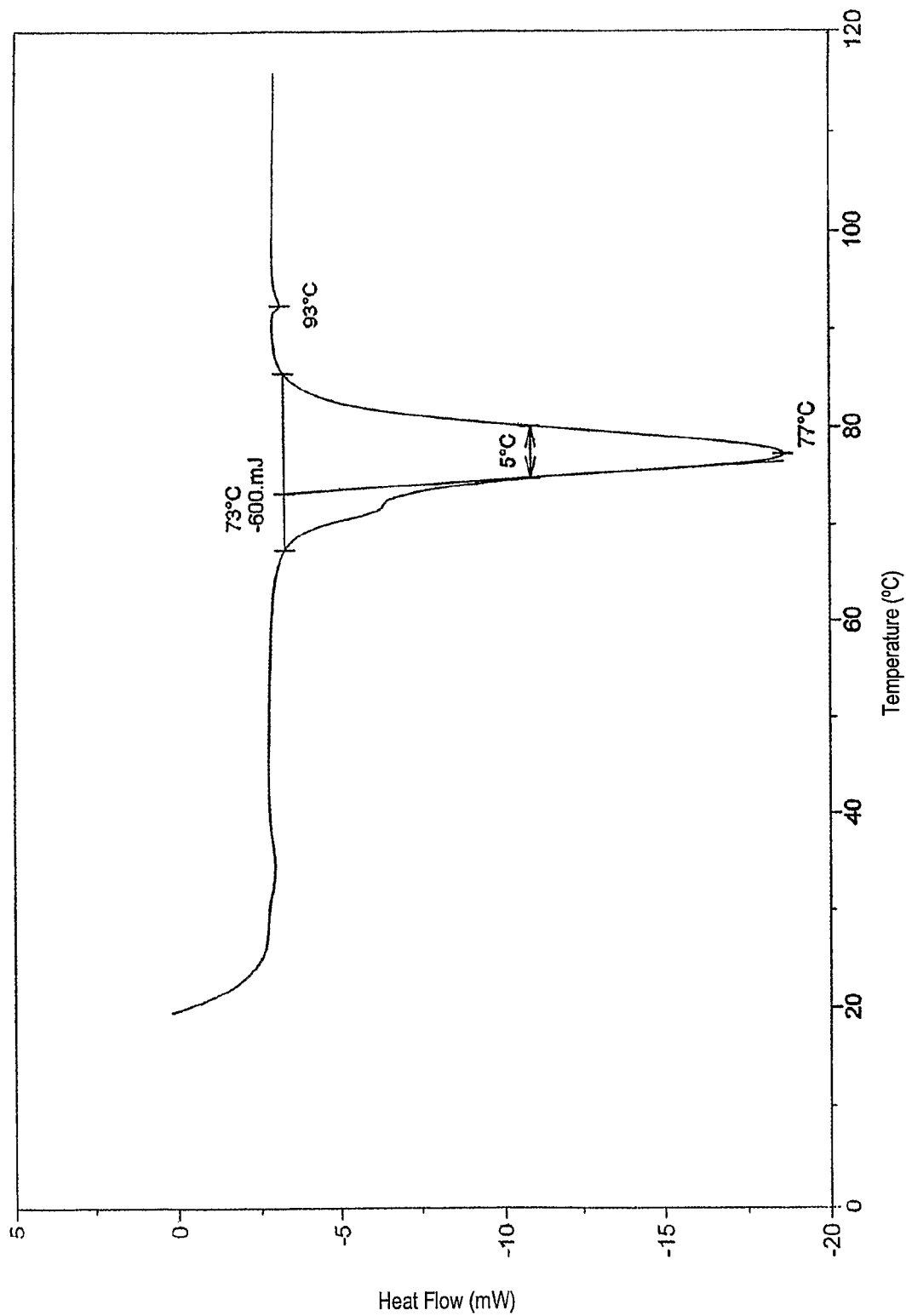

FIG. 2C shows the 50:50 blend of n-hexadecyl hexadecamide and n-lauryl lauramide, which exhibits a single melting peak at 77° C. having a broad onset shoulder. The shoulder indicates some incompatibility in packing of the two components into a single crystalline structure. Also, the blend is a eutectic blend, with a melting temperature (77° C.) lower than either of the individual components (95° C. for n-hexadecyl hexadecamide; 83° C. for n-lauryl lauramide).

Figure 2D:
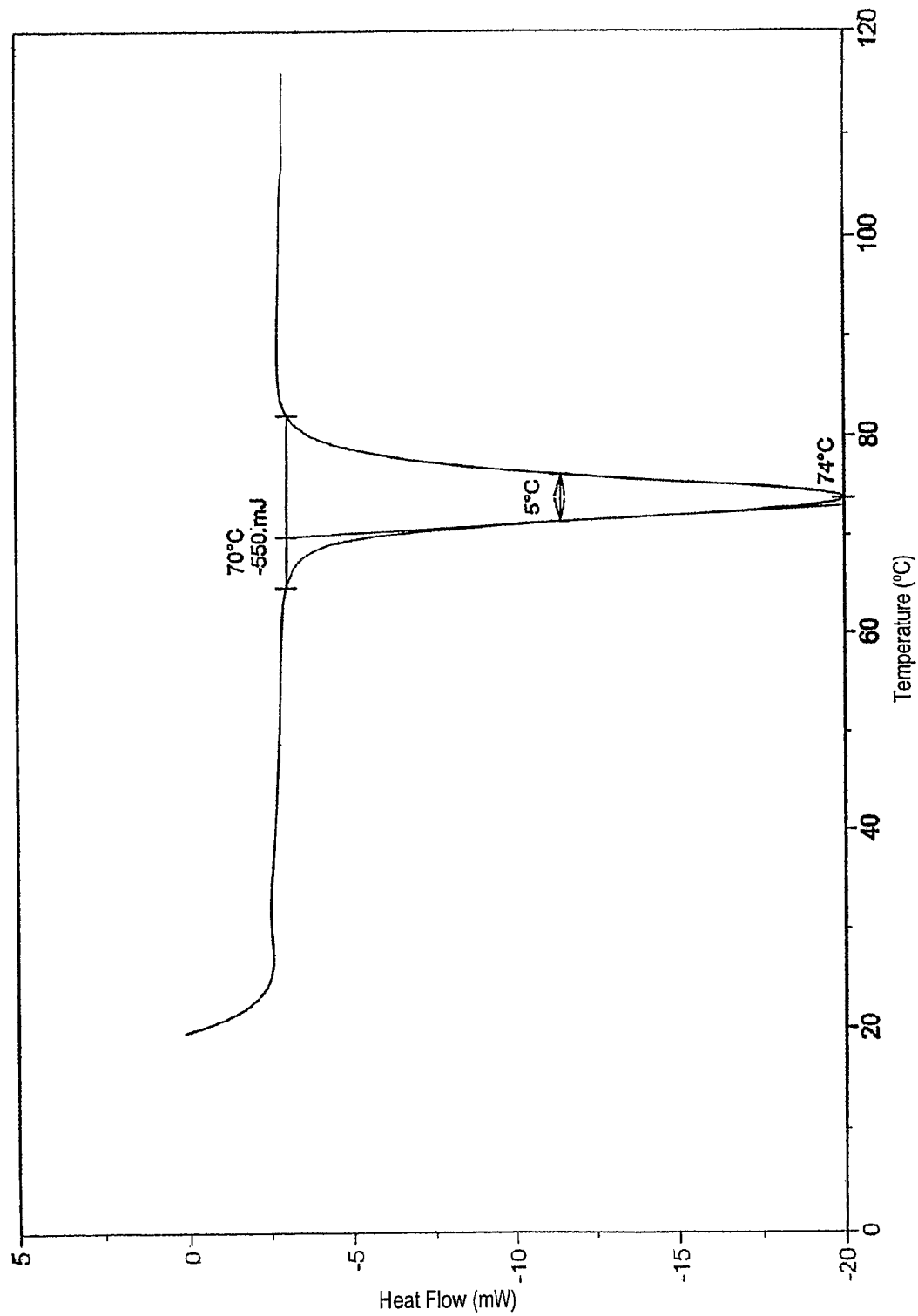
Figure 2E:
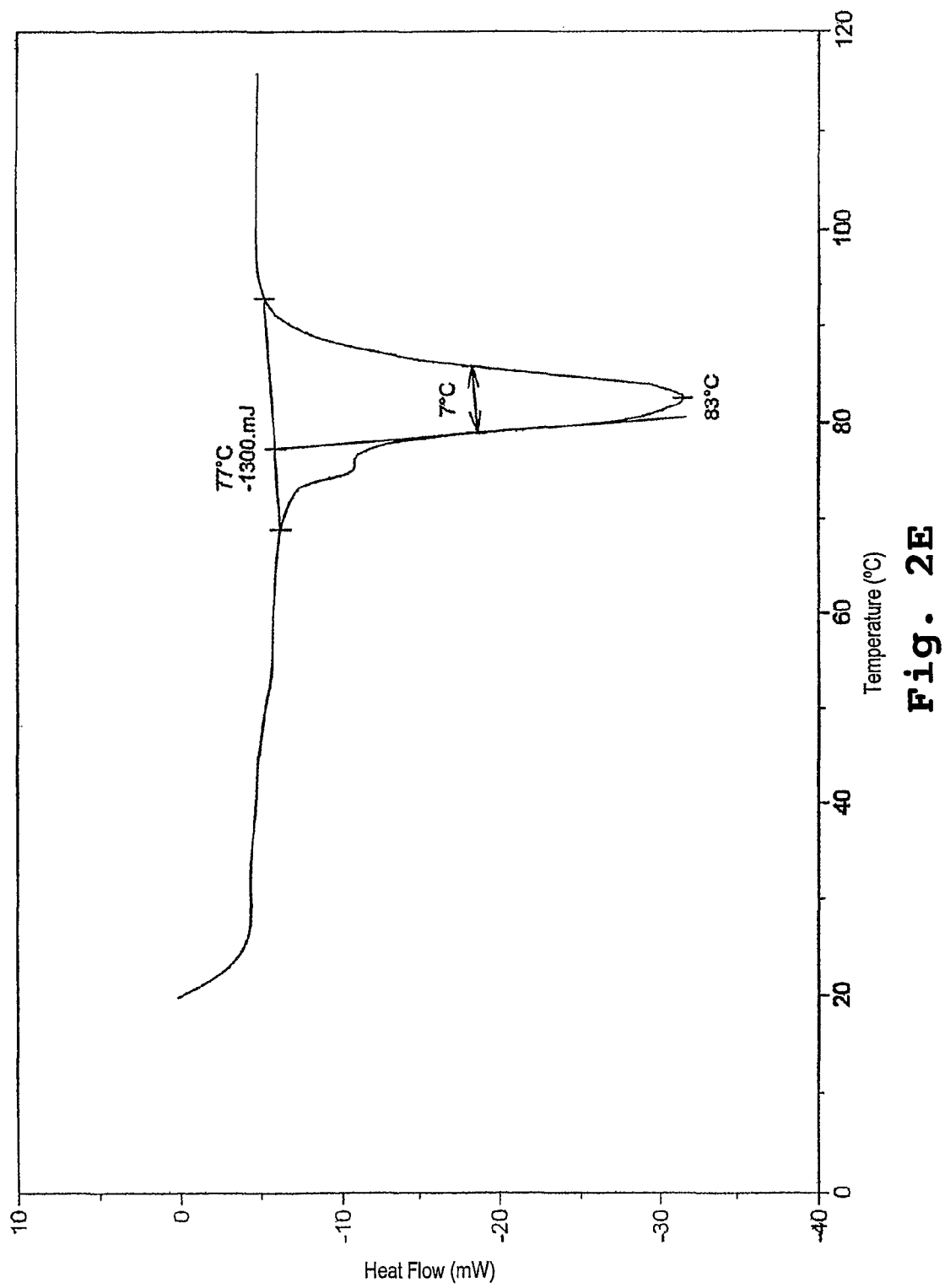

FIG. 2D shows the DSC scan for a 30:70 blend of n-hexadecyl hexadecamide and n-lauryl lauramide. A single, symmetrical peak at 74° C. corresponds to the melting point of the blend. Again, this blend is a eutectic blend.

In summary, the data in Table 5 and FIGS. 2A-2E illustrate that mixing two or more compounds that are structurally similar, e.g., both compounds are amides and differ in the carbon chain length by four to six carbon atoms, results in a significant broadening of the melting range and frequently results in multiple peaks (i.e., multiple melting points corresponding to each individual component). Such thermal properties are not acceptable for use in a thermo-mechanical device, where a single, sharp melting point is desired.

In another study, a series of aliphatic amide blends were prepared, where the materials differed by two carbon atoms per alkyl chain. Specifically, blends comprised of n-hexadecyl hexadecamide (N-16-16) and of n-stearyl stearamide (N-18-18) were prepared according to the procedure described in Example 1B. The blends and the weight percentage of each component are shown in the table presented in Example 2, below. The blends were characterized by DSC and the results are shown in FIG. 3 and in Table 6.

Figure 3:
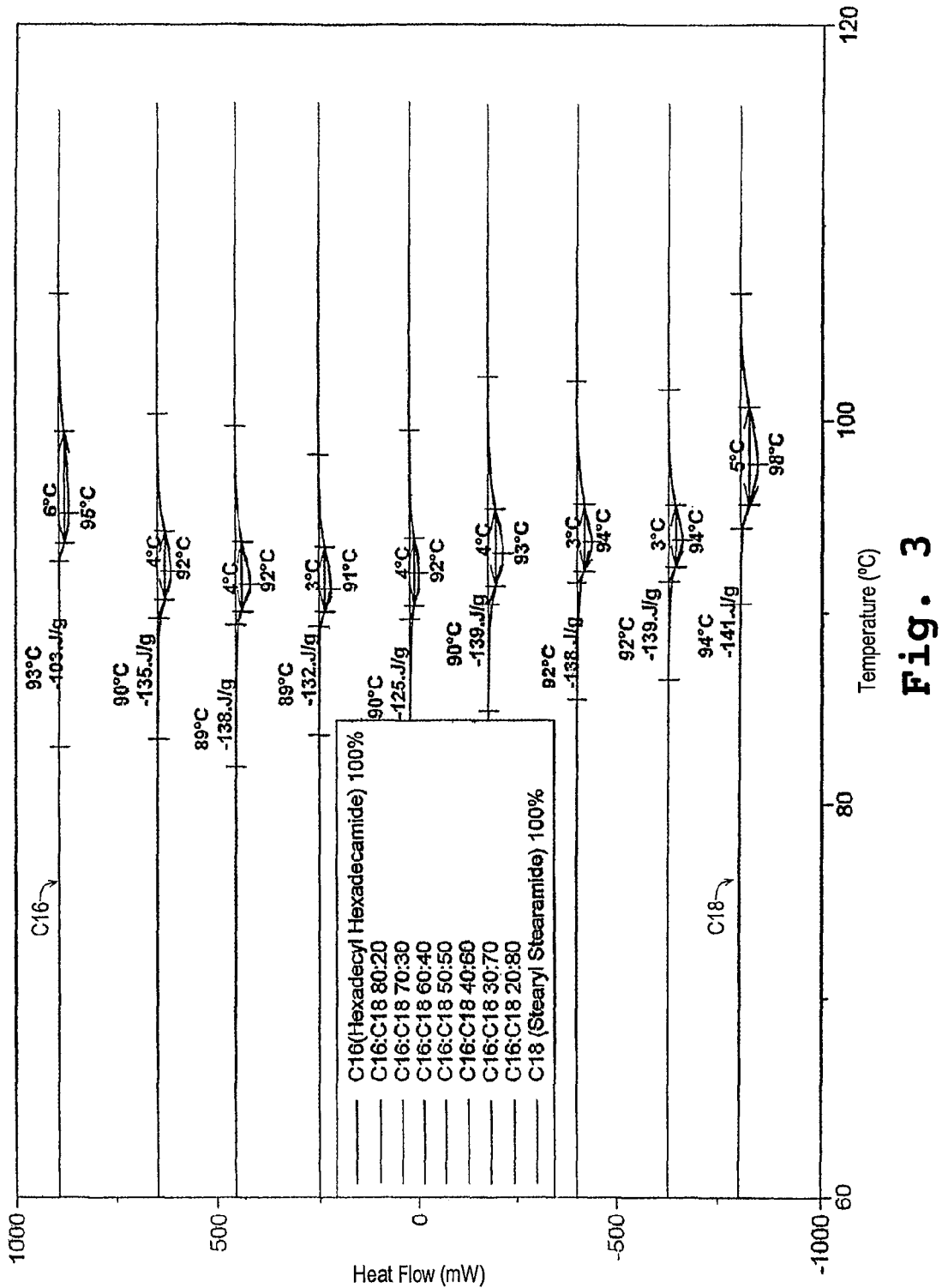
FIG. 3 shows DSC scans for n-hexadecyl hexadecamide and stearyl stearamide and for blends of n-hexadecyl hexadecamide/stearyl stearamide in weight ratios of 80:20, 70:30, 60:40, 50:50, 40:60, 30:70, 20:80.

FIG. 3 shows DSC scans for the individual neat components, n-hexadecyl hexadecamide and n-stearyl stearamide, and for blends of n-hexadecyl hexadecamide/stearyl stearamide in weight ratios of 80:20 (blend no. 12), 70:30 (blend no. 13), 60:40 (blend no. 14), 50:50 (blend no. 15), 40:60 (blend no. 16), 30:70 (blend no. 17), 20:80 (blend no. 18). All of the blends exhibited a single, sharp melting peak indicating that the individual components co-crystallize to form a miscible blend.

above illustrates that blends of aliphatic amide polymers provide the desired melting properties for use in a thermo-mechanical device when the two component amide polymers differ in the number of carbons in the alkyl tail attached either to the carboxyl moiety or to the nitrogen atom by an absolute value of less than four, i.e., by zero (0), one (1), two (2), or three (3).

Accordingly, compositions are provided that are comprised of two or more materials each having a structure of $R_n{}^1$—C(O)—NH—$R_n{}^2$ where n is an identifying integer corresponding to a material in the composition. For each material n in the composition, $R_n{}^1$ and $R_n{}^2$ are a saturated alkyl having between 7-22 carbon atoms, where for each material n $R_n{}^1$ and $R_n{}^2$ differ by one carbon atom. That is, the alkyl amide is symmetrical, e.g., have the same number of carbon atoms on either side of the nitrogen atom (counting the carbon in the carboxyl moiety as a carbon on the $R_n{}^1$ side of the nitrogen atom). In this aspect, the number of carbon atoms in $R_n{}^2$ of each material n differs by an absolute value of four or less.

In exemplary embodiments, the composition is first material (n=1) and a second material (n=2), wherein each of $R_1{}^1$ and $R_2{}^1$ are independently a saturated alkyl having between 9-19 carbon atoms, and each of $R_1{}^2$ and $R_2{}^2$ are independently a saturated alkyl having between 10-20 carbon atoms, wherein the number of carbon atoms in $R_1{}^1$ or $R_1{}^2$ is greater than the number of carbon atoms in $R_2{}^1$ or $R_2{}^2$, respectively, by one, two, three, or four. Alternatively, the composition is comprised of a first material (n=1) and a second material (n=2), wherein each of $R_1{}^1$ and $R_2{}^1$ are independently a saturated alkyl having between 9-19 carbon atoms, and each of $R_1{}^2$ and $R_2{}^2$ are independently a saturated alkyl having between 10-20 carbon atoms, wherein the number of carbon atoms in $R_1{}^2$ is greater than the number of carbon atoms in $R_2{}^2$ by two or four.

Specific exemplary compositions include those comprised of a first material (n=1) wherein $R_1{}^1$ is $CH_3(CH_2)_{10}$ and $R_1{}^2$ is $CH_3(CH_2)_{11}$ and of a second material (n=2) wherein $R_2{}^1$ is $CH_3(CH_2)_{14}$ and $R_2{}^2$ is $CH_3(CH_2)_{15}$; i.e., a blend of n-dodecyl dodecamide and n-hexadecyl hexadecamide.

Another example is a composition comprised of a first material (n=1) wherein $R_1{}^1$ is $CH_3(CH_2)_{16}$ and $R_1{}^2$ is $CH_3$

TABLE 6

| Composition Identification No.[1] | First Compound (wt %) | Second Compound (wt %) | Melting Point (° C.) | Melting Range (° C.) | Comment |
|---|---|---|---|---|---|
| 11 | N-18-18 (100) | N-16-16 (0) | 98 | 5 | Symmetrical |
| 12 | N-18-18 (80) | N-16-16 (20) | 94 | 3 | Symmetrical |
| 13 | N-18-18 (70) | N-16-16 (30) | 94 | 3 | Symmetrical |
| 14 | N-18-18 (60) | N-16-16 (40) | 93 | 4 | Symmetrical |
| 15 | N-18-18 (50) | N-16-16 (50) | 92 | 4 | Symmetrical |
| 16 | N-18-18 (40) | N-16-16 (60) | 91 | 3 | Symmetrical |
| 17 | N-18-18 (30) | N-16-16 (70) | 92 | 4 | Symmetrical |
| 18 | N-18-18 (20) | N-16-16 (80) | 92 | 4 | Symmetrical |
| 19 | N-18-18 (0) | N-16-16 (100) | 95 | 6 | Symmetrical |

[1]Refer to Example 1.A2 for additional details on blend compositions.

The data in Table 6 shows that a series of compositions having a sharp, defined melting transition, as evidenced by the single, symmetrical melting peak and the narrow melting range of 3-4° C., can be prepared from aliphatic amide polymer components having a difference in the number of carbon atoms in the alkyl tail attached to the carboxyl moiety of the amide (i.e., $R^1$–$R_2{}^1$) or in the alkyl tail attached to the nitrogen atom in the amide (i.e. $R^2$–$R_2{}^2$) has an absolute value of two. This result in combination with the study described $(CH_2)_{17}$ and of a second material (n=2) wherein $R_2{}^1$ is $CH_3(CH_2)_{12}$ and $R_2{}^2$ is $CH_3(CH_2)_{13}$, i.e., a blend of n-octadecyl octadecamide and n-tetradecyl tetradecamide.

Yet another example is a composition comprised of a first material (n=1) wherein $R_1{}^1$ is $CH_3(CH_2)_{14}$ and $R_1{}^2$ is $CH_3(CH_2)_{15}$ and of a second material (n=2) wherein $R_2{}^1$ is $CH_3(CH_2)_{12}$ and $R_2{}^2$ is $CH_3(CH_2)_{13}$, i.e., a blend of n-hexadecyl hexadecamide and n-tetradecyl tetradecamide.

Still another example is a composition comprised of a first material (n=1) wherein $R_1^1$ is $CH_3(CH_2)_{16}$ and $R_1^2$ is $CH_3(CH_2)_{17}$ and of a second material (n=2) wherein $R_2^1$ is $CH_3(CH_2)_{12}$ and $R_2^2$ is $CH_3(CH_2)_{13}$, i.e., a blend of n-octadecyl octadecamide and n-tetradecyl tetradecamide.

Further studies were conducted to provide compositions that melt over a wider temperature range and that have a more uniform variation in melting properties. As described in Example 2, polymers of the form $R^1$—C(O)—NH—$R^2$, where $R^1$ is aryl and $R^2$ is a saturated alkyl having between 8-22 carbon atoms were prepared. Polymer of this form are known as benzamides. Benzamide blends of n-octadecyl benzamide (C18 BZA) and n-hexadecyl benzamide (C16 BZA) were prepared and characterized by DSC. The results are shown in Table 7A and in FIGS. 4A-4E.

TABLE 7A

| Composition Identification No.[1] | First Compound (wt %) | Second Compound (wt %) | Melting Point (° C.) | Melting Range (° C.) | Comment re. DSC melting peak |
|---|---|---|---|---|---|
| 20 | C18 BZA | — | 88 | 5 | Symmetrical |
| 21 | C18 BZA (90) | C16 BZA (10) | 87 | 5 | Symmetrical |
| 22 | C18 BZA (80) | C16 BZA (20) | 83 | 7 | Symmetrical |
| 23 | C18 BZA (60) | C16 BZA (40) | 80 | 5 | Symmetrical |
| 24 | C18 BZA (50) | C16 BZA (50) | 79 | 4 | Symmetrical |
| 25 | C18 BZA (35) | C16 BZA (65) | 78 | 5 | Symmetrical |
| 26 | C18 BZA (20) | C16 BZA (80) | 79 | 5 | Symmetrical |
| 27 | C18 BZA (10) | C16 BZA (90) | 81 | 6 | Symmetrical |
| 28 | — | C16 BZA | 84 | 5 | Symmetrical |

[1]Refer to Example 2 for additional details on blend compositions.

The data in Table 7A shows that the C18 BZA/C16 BZA blends provide a continuously variable series of compositions that have sharp, distinct melting points. Moreover, the melting temperatures that can be created with the blends varies over a 10° C. range, permitting a commercially attractive series that allows a user to select a trigger or actuation temperature at approximately one degree intervals over the 78-88° C. range.

Figure 4A:
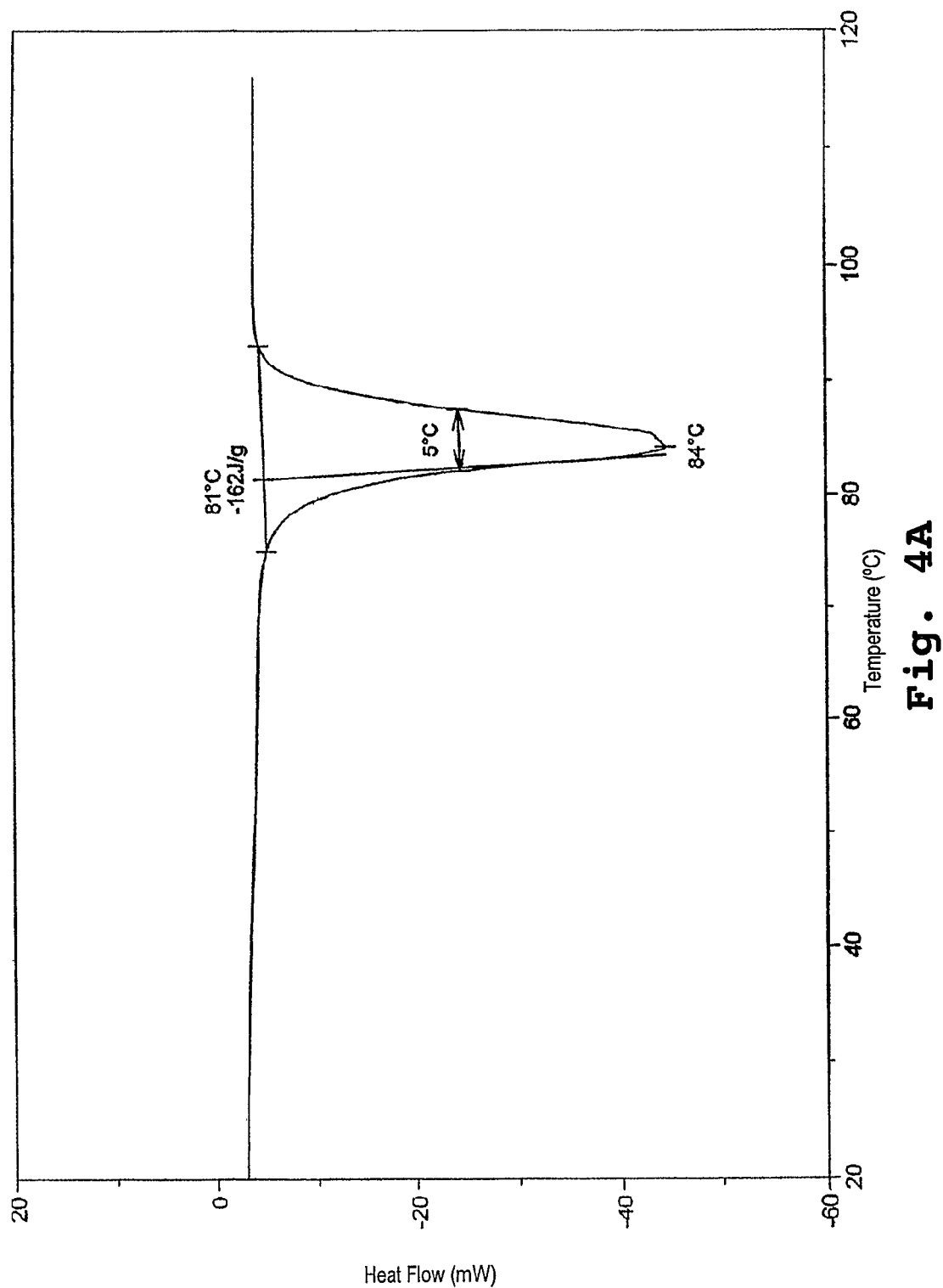
FIGS. 4A-4E are DSC scans of n-hexadecyl benzamide (FIG. 4A) and of octadecyl benzamide (FIG. 4E) and of blends comprised of octadecyl benzamide/n-hexadecyl hexadecamide in weight ratios of 70:30 (FIG. 4B), 50:50 (FIG. 4C), and 30:70 (FIG. 4D)
Figure 4B:
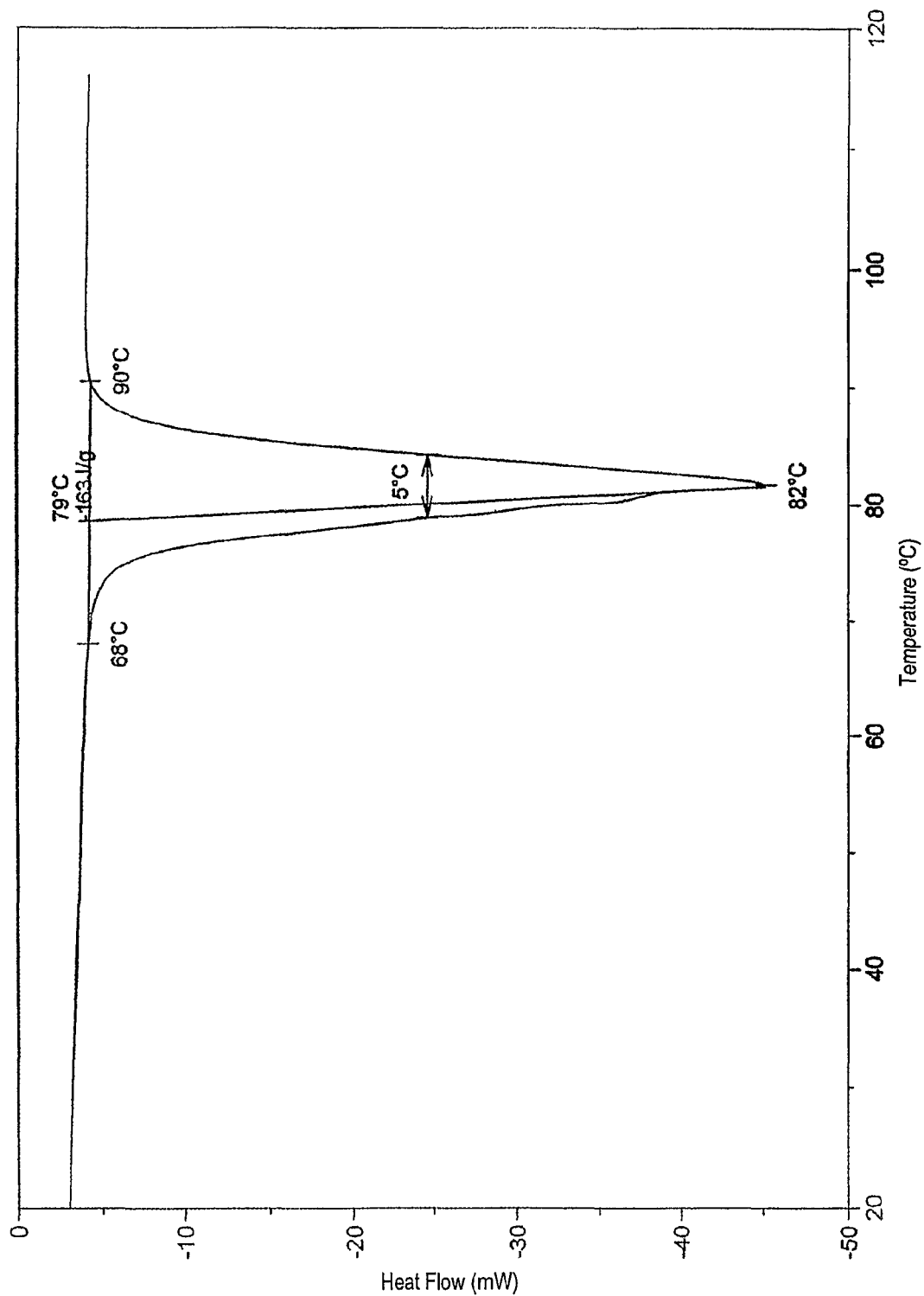
Figure 4C:
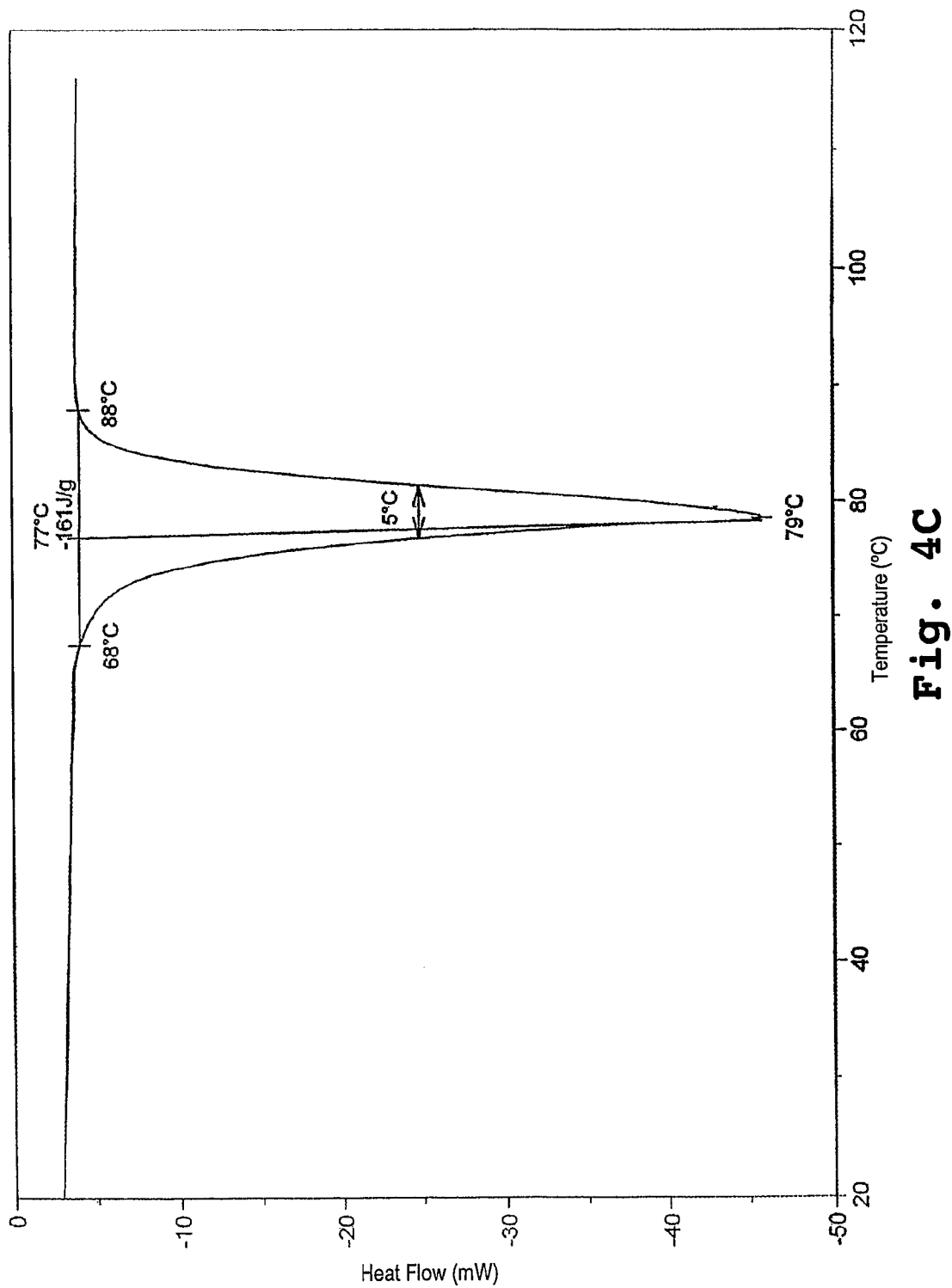
Figure 4D:
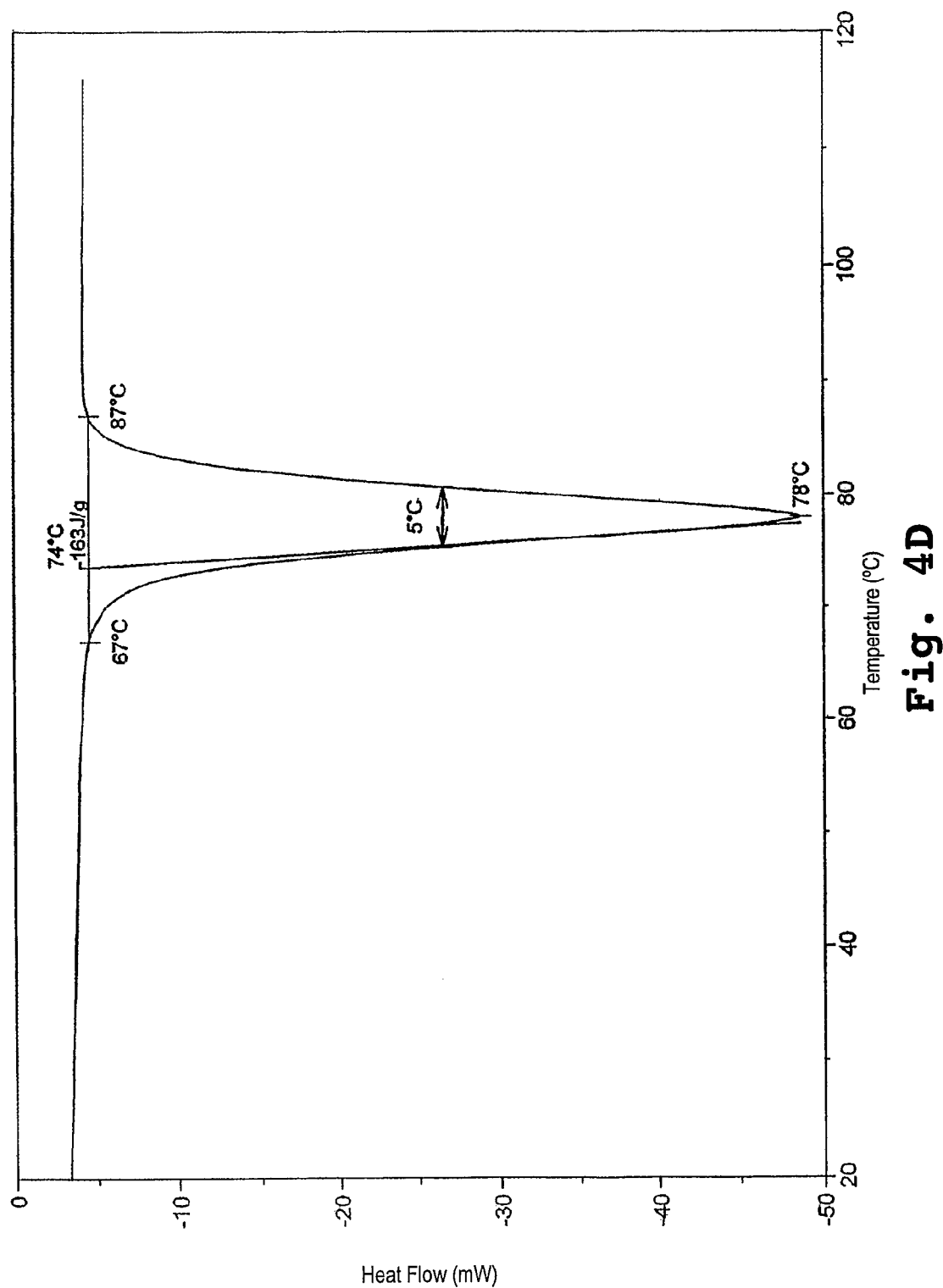
Figure 4E:
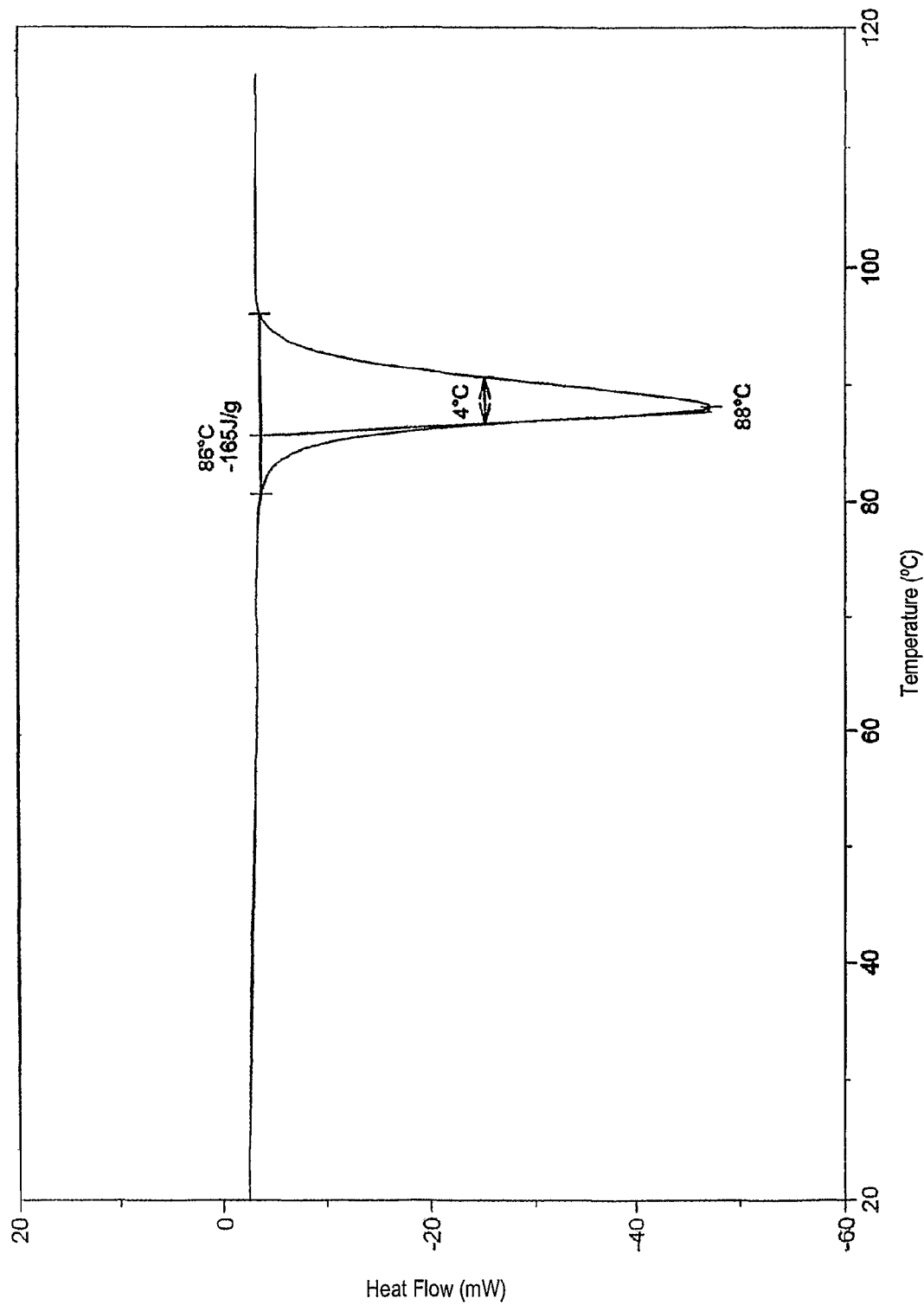

FIGS. 4A-4E shows the DSC scans for the two neat components, n-hexadecyl benzamide (C16 BZA, FIG. 4A) and octadecyl benzamide (C18 BZA, FIG. 4E), and of blends comprised of octadecyl benzamide/n-hexadecyl hexadecamide in weight ratios of 70:30 (FIG. 4B), 50:50 (FIG. 4C), and 30:70 (FIG. 4D). The neat components and each blend exhibit a single, sharp melting peak, indicative of a miscible polymer blend.

Figure 4F:
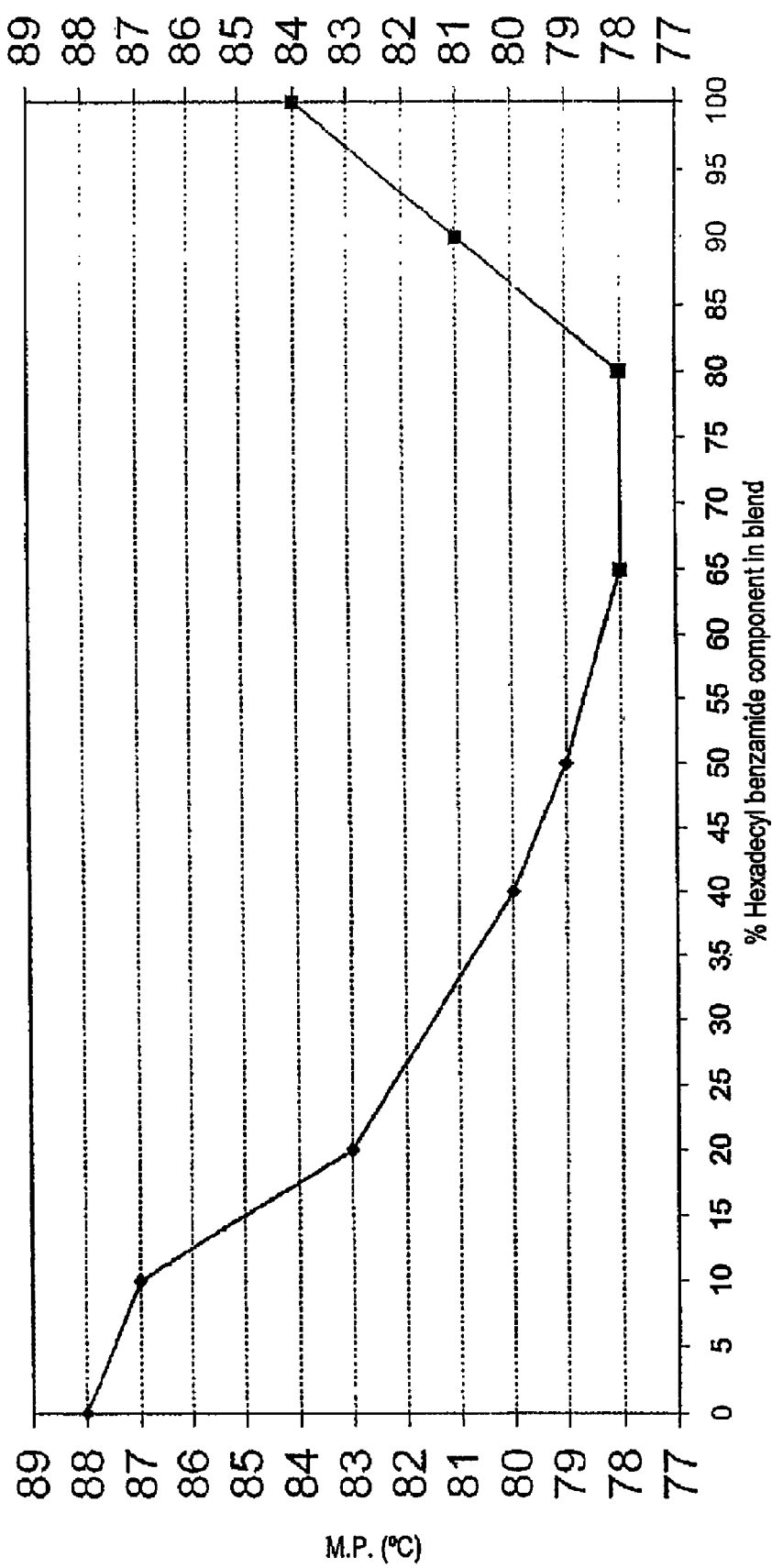
FIG. 4F shows the melting point, in ° C., as a function of percent n-hexadecyl benzamide (C16 BZA) for the compositions of FIGS. 4A-4E.

FIG. 4F shows the melting point, in ° C., as a function of percent n-hexadecyl benzamide (C16 BZA) in the compositions identified by nos. 20-28. Compositions with melting points of 88° C., 87° C., 84° C., 83° C., 80° C., 79° C., and 78° C. can be prepared from the two components. As evidenced by the DSC scans shown in FIGS. 4A-4E, the melting points are sharp and definite. The commercial attractiveness of this system can be appreciated, in that only two components are required to be kept in inventory to vary the activation temperature of an thermo-mechanical device over the range of 78-88° C.

Representative benzamide polymer blends were fabricated into thermo-mechanical devices according to the method of U.S. Pat. No. 4,170,956, incorporated by reference herein. One-hundred devices were prepared for each of the compositions identified as nos. 20-28. The average firing temperature and the range of temperature over which the devices triggered is reported in Table 7B.

TABLE 7B

| Identification No.[1] | First Compound (wt %) | Second Compound (wt %) | Trigger Temperature (° C.) | Trigger Temperature Range (° C.) |
|---|---|---|---|---|
| 20 | C18 BZA | | 80.6 | 1.1 |
| 21 | C18 BZA (90) | C16 BZA (10) | 82 | 1.7 |
| 22 | C18 BZA (80) | C16 BZA (20) | 78.5 | 2.2 |
| 23 | C18 BZA (60) | C16 BZA (40) | 76 | 1.1 |

TABLE 7B-continued

| Identification No.[1] | First Compound (wt %) | Second Compound (wt %) | Trigger Temperature (° C.) | Trigger Temperature Range (° C.) |
|---|---|---|---|---|
| 24 | C18 BZA (50) | C16 BZA (50) | 75 | 1.7 |
| 25 | C18 BZA (35) | C16 BZA (65) | 72.6 | 1.1 |
| 26 | C18 BZA (20) | C16 BZA (80) | 74.4 | 2.8 |
| 27 | C18 BZA (90) | C16 BZA (90) | 77 | 1.1 |
| 28 | — | C16 BZA | 85 | 2.2 |

[1]Refer to Example 2 for additional details on blend compositions.

As can be seen, this series of compositions all exhibit a narrow trigger temperature range of less than about 3° C. at the temperature indicated. Accordingly, devices that accurately respond at a definite temperature can be manufactured from blends of benzamides, where the alkyl chain attached to the nitrogen moiety ($R^2$, $R_2^2$) differ by an absolute value of less than about 4, preferably less than about 3.

Figure 5A:
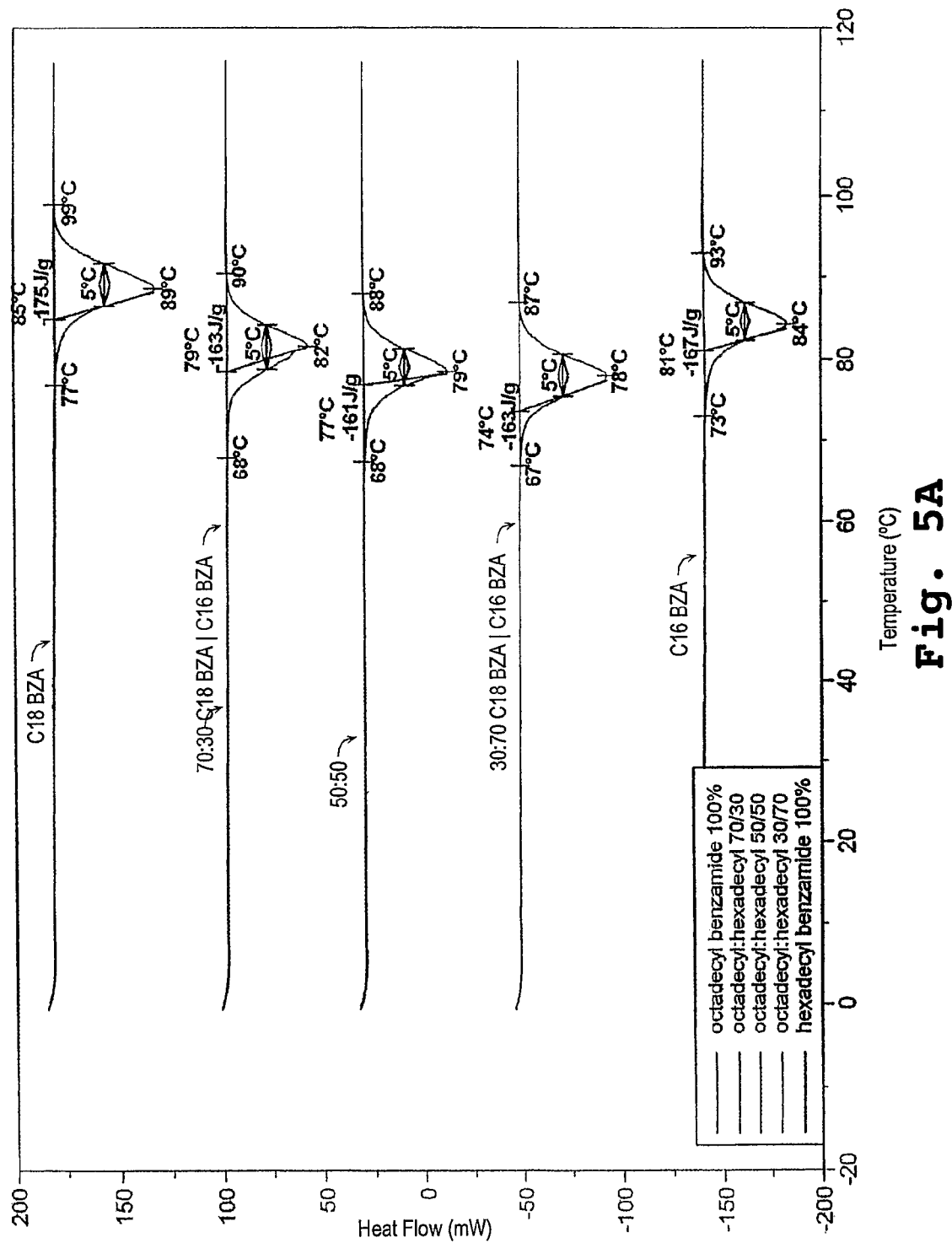
FIG. 5A shows DSC scans for n-octadecyl benzamide, n-hexadecyl hexadecamide and for blends of the two in weight ratios of 70:30, 50:50, and 30:70.
Figure 5B:
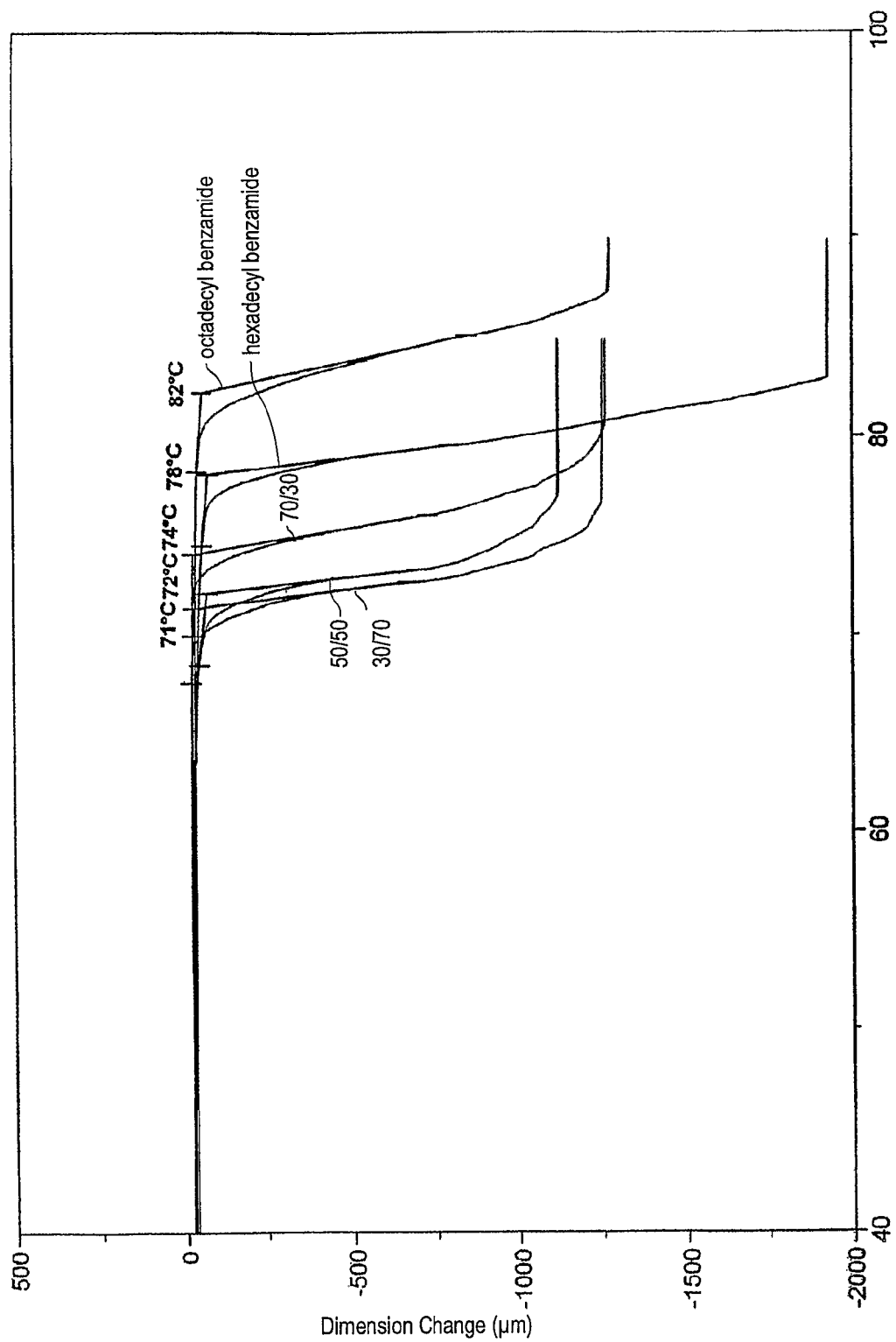
FIG. 5B shows the change in dimensions, in micrometers (μm), as a function of temperature, in ° C., as measured by thermal mechanical analysis (TMA) for n-octadecyl benzamide, n-hexadecyl hexadecamide and for blends of the two in weight ratios of 70:30, 50:50, and 30:70.

In another study, a similar series of n-octadecyl benzamide (C18 BZA)/n-hexadecyl benzamide (C16 BZA) blends was prepared in weight ratios of 70:30, 50:50, and 30:70. The blends and the neat components were characterized by DSC and the scans are shown in FIG. 5A. A single, distinct melting peaks for each blend is observed. The same compositions were analyzed by thermal mechanical analysis to evaluate the mechanical properties, useful to ascertain the suitability of the composition in a thermo-mechanical device. FIG. 5B shows the TMA analysis, where the change in dimension, in micrometers (μm), as a function of temperature, in ° C., is shown for n-octadecyl benzamide, n-hexadecyl hexadecamide and for blends of the two in weight ratios of 70:30, 50:50, and 30:70.

Example 3 describes another study where compounds of the form $R^1$—C(O)—NH—$R^2$, where $R^1$ is a saturated alkyl having between 8-22 carbon atoms and $R^2$ is aryl, were prepared. Compounds of this form are known as n-alkyl anilides. Blends of n-alkyl anilides having 12 or 14 carbon atoms in the moiety attached to the nitrogen atom were prepared and characterized by DSC. The results are shown in Table 8.

TABLE 8

| Identification No.[1] | First Compound (wt %) | Second Compound (wt %) | Melting Point (° C.) | Melting Range (° C.) | Comment re. DSC melting peak |
|---|---|---|---|---|---|
| 29 | C14 ANA (100) | C12 ANA (0) | 89 | 6 | Symmetrical |
| 30 | C14 ANA (70) | C12 ANA (30) | | | Symmetrical |
| 31 | C14 ANA (50) | C12 ANA (50) | | | Symmetrical |
| 32 | C14 ANA (70) | C12 ANA (30) | | | Symmetrical |
| 33 | C14 ANA (0) | C12 ANA (100) | | 5 | Symmetrical |
| 34 | C14 ANA (50) | Stearone (50) | 73 | 8 | Broad onset second heat hysteresis |
| 35 | C14 ANA (50) | C18 BZA (50) | | | broad |

[1]Refer to Example 3 for additional details on blend compositions.

The data in Table 8 shows that blends of n-alkyl analides can be prepared which exhibit a single, sharp melting point and a narrow melting range of less than about 6° C., when the number of carbon atoms in the alkyl chain attached to the carboxyl moiety in the first alkyl analide differs from the number of carbon atoms in the alkyl chain attached to the carboxyl moiety in the second alkyl analide by an absolute value of less than about four. For example, in the blends identified above as nos. 30-33, the number of carbon atoms in the alkyl chains $R^1$ and $R_2^1$ differ by an absolute value of two.

The blends identified as nos. 34 and 35 illustrate that mixtures of analides with alkyl ketones or with benzamides do not provide miscible blends.

III. Devices

In another aspect, devices comprised of a material having the structure $R^1$—C(O)—NX—$R^2$ are provided, wherein each of $R^1$ and $R^2$ is independently a saturated alkyl having between 7-22 carbon atoms or an aryl, X is H or C(O)—Y, Y together with $R^1$ forms a ring. In one embodiment, the device has a temperature range over which a trigger temperature occurs of less than about 5° C., more preferably of less than about 3° C., still more preferably of less than about 2° C. Alternatively, the material in the device, when tested by TMA exhibits a softening range (defined as approximately T ½ minus T onset) and undergoes a dimensional change over a temperature range of less than about 5° C., more preferably of less than about 3° C., still more preferably of less than about 2° C., when subjected to a constant force, for example a force of about 0.5 Joule/meter and a heating increase of 1° C./minute.

Materials contemplated for use in a device include the alkyl amides, blends of alkyl amides, benzamides, blends of benzamides, n-alkyl analides, and blends of n-alkyl anilides, all discussed above. Specifically, and with respect to the alky amides, devices comprising a material of the form $R^1$—C(O)—NH—$R^2$, wherein each of $R^1$ and $R^2$ is independently a saturated alkyl having between 7-22 carbon atoms and wherein the number of carbon atoms in $R^1$ and $R^2$ differs by an absolute value of less than four, i.e., by 3, 2, 1, or 1. Specific examples include n-dodecyl dodecamide, n-dodecyl decamide, d-octadecyl octadecamide, n-hexadecyl hexadecamide, and octadecyl docosanoicamide (behenicamide, C22).

Devices comprising blends of n-alkyl amides are also contemplated, where the device comprises a first material of the form $R^1$—C(O)—NH—$R^2$ and a second material of the form $R_2^1$—C(O)—NH—$R_2^2$, where $R^1$ and $R^2$ are as described above and $R_2^1$ and $R_2^2$ are as described for $R^1$ and $R^2$, respectively. The number of carbon atoms in $R_2^2$ differs from the number of carbon atoms in $R^2$ by an absolute value of four or less. Alternatively, in another embodiment, the number of carbon atoms in $R^1$ or $R^2$ differs from the number of carbon atoms in $R_2^1$ or $R_2^2$, respectively, by one, two, three, or four. Specific examples include blends of n-dodecyl dodecamide and n-hexadecyl hexadecamide; n-octadecyl octadecamide and n-tetradecyl tetradecamide; n-hexadecyl hexadecamide and n-tetradecyl tetradecamide; n-octadecyl octadecamide and n-hexadecyl hexadecamide; and n-octadecyl octadecamide and n-docosanoic docosanoicamide.

More generally, a blend is comprised of two components, identified as component A and component B. A and B are compounds dependently selected from the group consisting of linear alkyl amides, benzamides, and anilides; that is A and B are both a linear alkyl amide, or are both a benzamide, or are both an anilide. However, while A and B are from the same general family of compounds (e.g., both are benzamides, or both are alkyl amides, etc.), A and B can individually differ in carbon number by an absolute value of from 2 to 4. Thus, the carbon chain lengths in the aliphatic portions of the components can differ. A and B are present in a ratio of from 90:10 to 10:90. Also, it is preferred that A and B individually have a purity of greater than 95 wt %. Component purity can be measured by a variety of techniques known to those of skill, such as DSC and chromatography. Common impurities include alkyl amine, alkyl nitrile, and amic acid and preferably the composition contains less than 0.5 wt % of collectively of alkyl amine, alkyl nitrile, and amic acid.

Devices comprising a component prepared from a benzamide compound or a benzamide compound blend are also contemplated. Here, the component is prepared from a material of the form $R^1$—C(O)—NH—$R^2$ where $R^1$ is aryl and $R^2$ is a saturated alkyl having between 8-22 carbon atoms. Blends of benzamides include a second material of the same form, $R_2^1$—C(O)—NH—$R_2^2$, where $R_2^1$ is aryl and $R_2^2$ is a saturated alkyl having between 8-22 carbon atoms. The number of carbon atoms in $R_2^2$ differs from the number of carbon atoms in $R^2$ by an absolute value of four or less. A specific example is where $R^2$ is $CH_3(CH_2)_{15}$ and $R_2^2$ is $CH_3(CH_2)_{17}$.

Devices comprising a component prepared from an n-alkyl anilide or a n-alkyl anilide blend are also contemplated. Here, the component is prepared from a material of the form $R^1$—C(O)—NH—$R^2$ where $R^1$ is a saturated alkyl having between 8-22 carbon atoms and $R^2$ is aryl. Blends of n-alkyl anilides include a second material of the same form, $R_2^1$—C(O)—NH—$R_2^2$, where $R_2^1$ is a saturated alkyl having between 8-22 carbon atoms and $R_2^2$ is aryl. The number of carbon atoms in $R_2^1$ differs from the number of carbon atoms in $R^1$ by an absolute value of four or less, excluding zero. In one embodiment, $R^1$ is a saturated alkyl having between 14-20 carbon atoms and $R_2^1$ is a saturated alkyl having between 14-20 carbon atoms, wherein the number of carbon atoms in $R_2^1$ differs from the number of carbon atoms in $R^1$ by an absolute value of one, two, or three. A specific example of a blend of n-alkyl anilides is where $R^1$ is $CH_3(CH_2)_{12}$ and $R_2^1$ is $CH_3(CH_2)_{10}$ (i.e., a C14 ANA/C12 ANA blend).

Various devices comprising at least one component prepared from one of the above described materials are contemplated. Thermo-mechanical devices that are activated at a specific temperature are known in art, as described in the background section above. Passive devices formed of the materials described herein are also contemplated, and an exemplary device in the form of a water storage tank is described below. Typically, when the environment in which the device is in use reaches a certain temperature, the component part prepared from the material undergoes its melt transition, thereby inducing a reaction in the device or a desired outcome. A reaction can be to open or close a circuit or a valve, to induce movement of an adjacent part in the device, to cause movement of the component itself, and the like.

Exemplary thermo-mechanical devices are described in U.S. Pat. Nos. 4,170,956; 5,537,950; 6,403,131; 6176,197; 4,289,088; 5,495,865; 4,896,728; 4,006,780; 5,988,102; and 5,025,627, each of which are incorporated by reference herein. In general terms, a thermo-mechanical actuator, comprises, a fixed member comprised of a material that responds to a change in temperature by a change in volume, such as the materials described here. The actuator also includes at least one moveable member coupled to or adjacent to the fixed member. As the environment of use increases or decreases, the material undergoes a phase transition, such as a melting point, that causes a change in volume of the material. Due to this change in volume, the moveable member is induced to move, which directly or indirectly results in activation of the actuator.

In another embodiment, the compositions described herein are used as a phase change material for thermal energy storage. The phase change material is capable of absorbing and/or releasing heat energy as the material undergoes its melting transition. For example, a device such as a water storage reservoir, e.g., a reservoir in a water heater, can be prepared to include one or more of the compositions described above. A specific example would be a water reservoir formed to include a lining prepared from a 90:10 mixture of C16 BZA: C18 BZA, which has a melting point of 80° C. and a heat capacity of about 2 J/g. As water in the reservoir is heated from, for example 50° C. to 80° C., about 60 Joules of energy is stored. When the water reaches 80° C., an additional 200 Joules is stored as the benzamide mixture undergoes its melt transition at 80° C. The total energy stored in heating water 30° C. is about 260 J/g. In contrast, in a conventional water heater reservoir, water warmed from 50° C. to 80° C. results in about 120 J/g of energy stored, based on the heat capacity of water of about 4 J/g.

In another example, microcapsules can be formed of the compositions described herein and used in applications for storage and/or release of heat energy. The microcapsules can be incorporated into materials or can be dispersed in fluids. The high surface area to volume ratio of microcapsules facilitates heat flow into and out of the material or fluid in which they are incorporated. Microcapsules can be prepared by any of a variety of well known methods, including for example, interfacial polymerization or coacervation. Microcapsules in the range of about 10-1000 microns are preferred.

In another embodiment, a device is formed or includes a component part formed of a composition as described above, the composition additionally including an inorganic filler or an insoluble nucleating agents incorporated into the temperature-responsive composition. In many thermo-mechanical devices, the temperature-responsive component prepared from the temperature-responsive composition is held in place, e.g., is biased or under a shear stress, for a prolonged period of time. It is desirable that the component exhibit low creep under such shear and holding conditions, otherwise premature triggering can occur. A standard method to test the strength of the component is to make a device and subject it to a load test below the trigger temperature of the component part. Also, it is desired in some devices that the temperature-responsive component prepared from the temperature-responsive composition be thermally conductive. Materials that are poorly thermally conductive often melt over a wider range of temperature than predicted, particularly when the device and/or the component is relatively large and it takes time for heat to be transmitted throughout the device and/or the component. Incorporation of an inorganic filler into the temperature-responsive composition will increase the effective strength and shear resistance of the material. The filler may be incorporated in an amount typically between about 5% w/w and 35% w/w. Also, the addition of a filler that exhibits good thermal conductivity aids in increasing the strength of the material, while decreasing the effective temperature melting range due to improved conductivity. Of particular utility are particulate inorganic materials that a) have a particle size between about 1 micron and 200 microns, b) a thermal conductivity (k) greater than about 10 W/m·K. Specific examples of suitable fillers include, but are not limited to, boron nitride (k=300+W/m·K at 25° C.), calcium carbonate, wollastonite (calcium metasilicate, $CaSiO_3$; k=15 W/m·K), zinc oxide k=10 W/m·K), magnesium oxide (k=37 W/m·K at 26° C.), aluminum nitride (k=260 W/m·K at 25° C.), and aluminum oxide (k=30 W/m·K at 25° C.).

In another embodiment, addition of a nucleating agent to the composition is contemplated. Because some organic compounds, even when very pure, crystallize slowly use of such organic compounds in a thermo-mechanical device requires that the device after assembly with a component prepared from such an organic compound be kept physically restrained until the organic compound has crystallized and hardened sufficiently. This can be particularly problematic when making devices with relatively low trigger temperatures where it would be expected that crystallization would take longer than for higher melting compounds. This potential problem can be alleviated by adding an insoluble nucleating agent to the polymer to increase the rate of crystallization, thus permitting more rapid handling of manufactured parts. Suitable nucleating agents include inorganic materials, such as boron nitride, calcium carbonate, mica, and similar materials, as well as insoluble organic materials such as benzoate salts (Na, K). These materials need be present only in very small amounts, typically less than 1%.

Figure 6B:
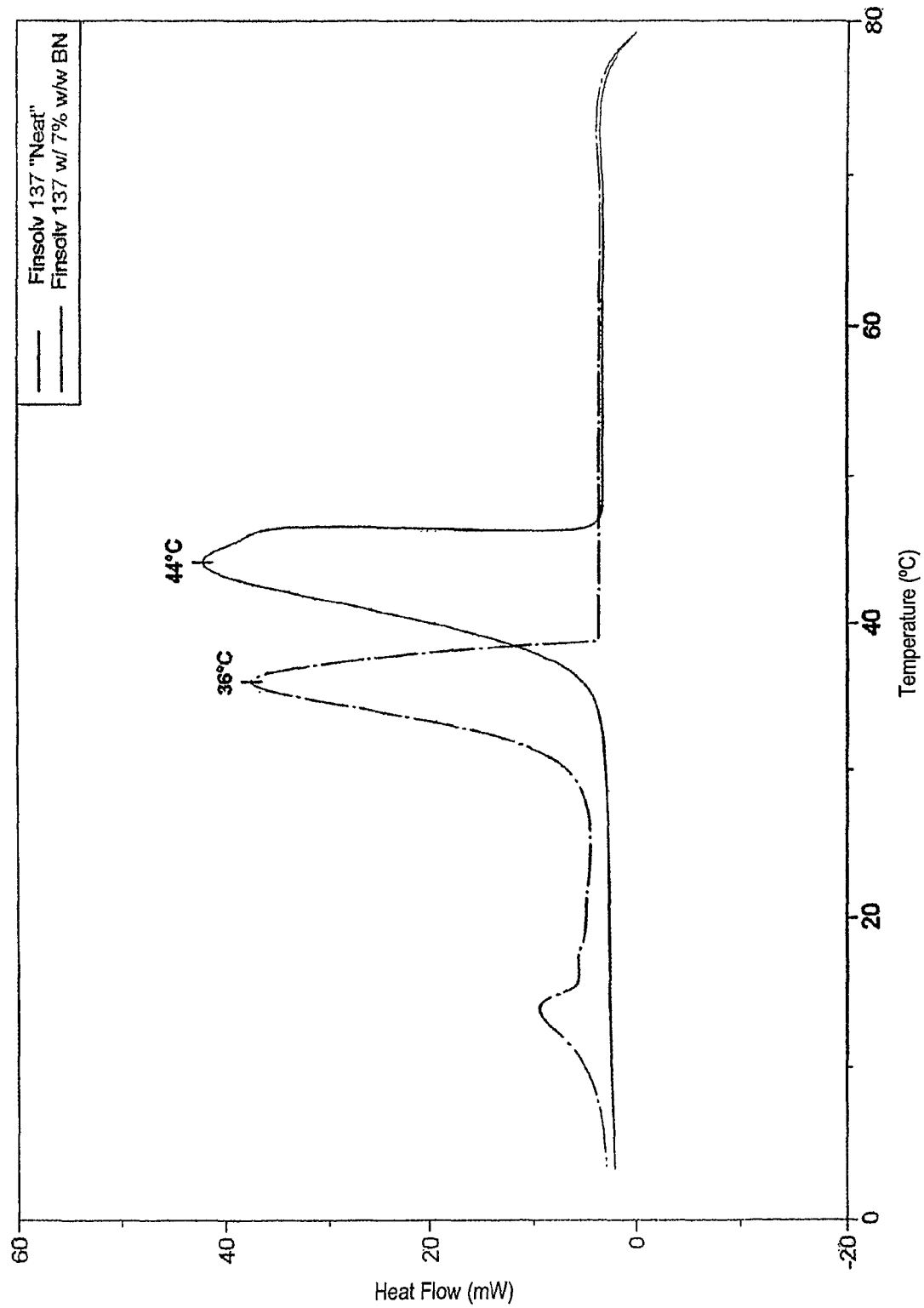

To illustrate these embodiments, compositions were prepared using behenyl benzoate (FINSOLV® 137, Finetex Inc. (Elmwood Park, N.J.)) with boron nitride incorporated as a filler and as a nucleating agent. As seen in the DSC scans in FIGS. 6A-6B, neat behenyl benzoate has a melting point of 57° C. (FIG. 6A) and crystallizes at 36° C. (FIG. 6B) making it difficult to use in production. Addition of 7% boron nitride (PolarTherm® 120, GE Advanced Ceramics, Cleveland, Ohio) did not alter the melting point (see FIG. 6A) but increased the crystallization temperature to 44° C. (see FIG. 6B), an improvement of 8° C. when measured at 10° C. per minute.

Figure 7:
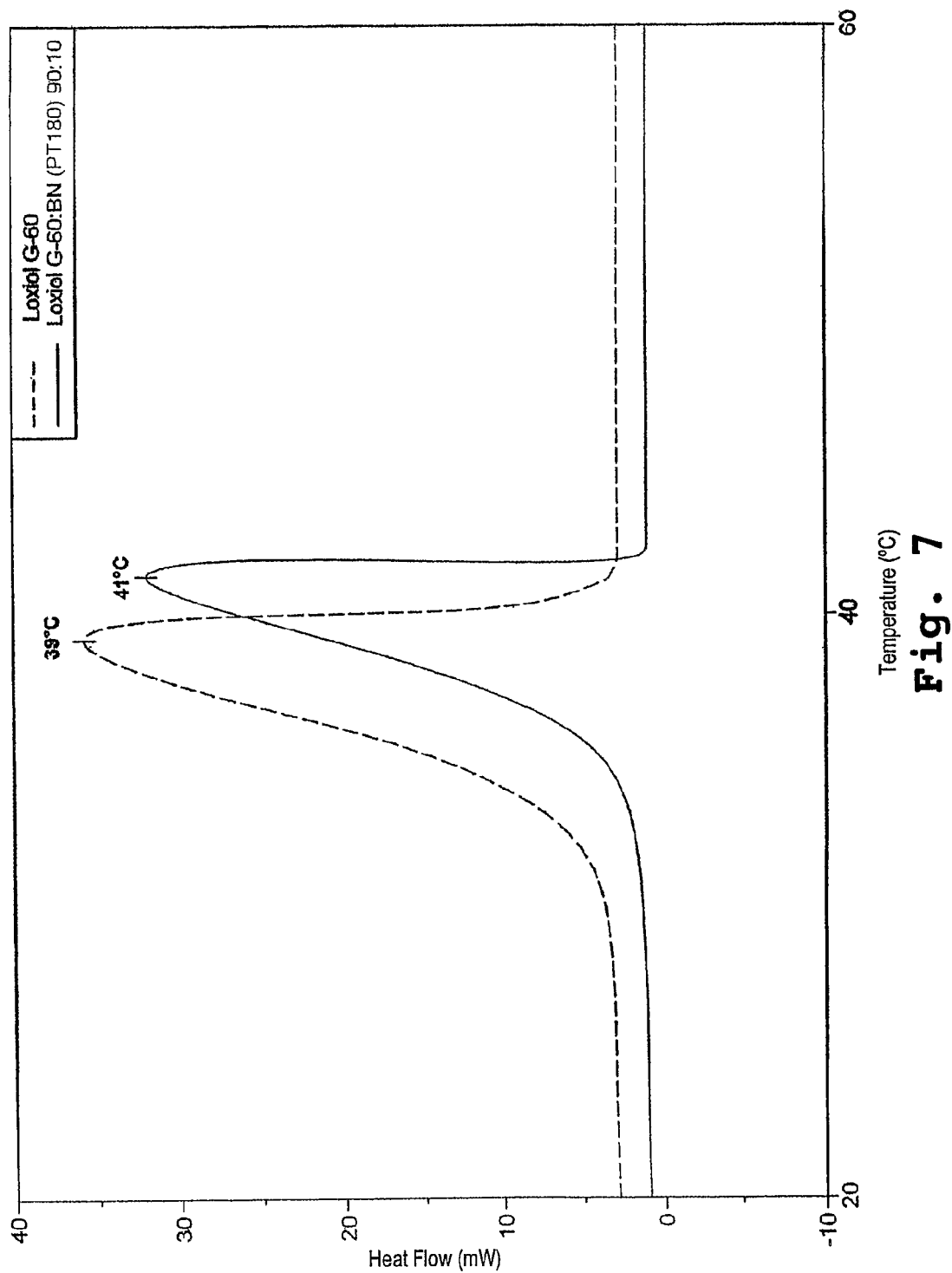
FIG. 7 is a cooling DSC scan for di-octadecyl phthalate neat and with addition of boron nitride.

A second composition was prepared with di-octadecyl phthalate (Loxiol® G60, Cognis Corp. USA, Cincinnati, Ohio) with addition of boron nitride. Di-octadecyl phthalate has a melting point of 50° C., and as seen in FIG. 7, crystallizes at 39° C. The slow recrystallization makes it difficult to use in production. Addition of 10% w/w of the boron nitride increased the crystallization temperature to 41° C.

In another aspect, the compositions described herein also find use as a visual indicating component in a device, and more generally, as a means for visually indicating attainment of a selected temperature. Devices, or portions of devices, designed to signal that a certain minimum or maximum temperature in an environment has been reached are used in many fields, including but not limited to the food industry, the transportation industry, research laboratories, medical fields, industrial processes, etc. Use of the materials described herein in visual temperature indicating elements is illustrated in Examples 4 and 5. As described in Example 4, a visual indicating element was fabricated from a mixture of 90 weight percent C18 BZA and 10 weight percent C16 BZA. The mixture when below its melting point of 82° C. scatters light and is opaque white. The mixture was applied to a clear substrate. The coated substrate was mounted onto a paper having a red circle to form a laminated device, the coated portion of the substrate obscuring the red circle such that the red circle was not visible. When the laminated device was placed in an environment heated to 85° C., the red circle was visible as the C18/BZA/C16 BZA mixture melted and became transparent.

Another temperature indicating device was constructed, as described in Example 5. A mixture of C18 BZA/C16 BZA (90:10) was crystallized and collected as a white powder. The powder was mixed with an epoxy resin to form an opaque white resin composite. The resin was applied to a transparent substrate and dried. When the substrate was placed in an environment heated to 85° C., the film of resin became transparent. The substrate was removed from the warm environment and the film became opaque.

Thus, the materials are suitable for use in single-use and in reusable devices to signal a user that a certain temperature has been attained. The single, sharp melting point of the materials permits accurate, selectable indication of attainment of a selected temperature. The materials are opaque below their melting point, and become transparent above their melting point, so that a signal that is initially obscured by the opaque material becomes visible as the material becomes transparent. It will be appreciated that because the materials can be blended in various ratios compositions can be prepared that have a wide range of melting temperatures. Typical uses in the food industry and transport industries include devices that sense temperatures in the range of about 60-100° C., more specifically in the range of 75-95° C.

In one embodiment, a device is comprised of a substrate that contains on at least a portion thereof, an indicating element visible to the human eye. The indicating element can take many forms, for example, a dot of color, a written word or number, a graphic, a transparent region, etc. The indicating element is obscured by a temperature-responsive member, the member comprised of a material or blend of materials described above. The temperature-responsive member obscures the indicating element with the material from which the temperature-responsive member is below its melting point, where the material is opaque and scatters light. When the temperature-responsive member is subjected to a temperature at or near the melting point of the material from which it is fabricated, it becomes transparent, exposing the indicating element. It will be appreciated that the indicating element and the temperature-responsive member can be directly adjacent or can be separated by one or more intervening layers of a transparent material, which can be a gas, a liquid, or a solid.

IV. Examples

The following examples are illustrative in nature and are in no way intended to be limiting.

Methods

Melting points were measured using a TA Instrument Differential Scanning Calorimeter. Unless otherwise noted the heating and cooling rate was 10° C. per minute. Melting point ranges are defined as the peak width at ⅓ height when heated at a rate of 10° C. per minute.

Triggering temperature ranges were measured by preparing spring-loaded test devices and heating the devices at a rate of 1° C. per minute. The number of devices that fire was measured over 1° F. intervals and the average firing temperature and range was recorded. Triggering temperatures can also be evaluated using TMA.

Comparative Example 1

Organic eutectic mixtures as described in U.S. Pat. No. 5,537,950 were prepared by combining stearone (($C_{17}H_{35}$)—C(O)—($C_{17}H_{35}$)) and stearyl stearamide (n-octadecyl octadecamide; $CH_3(CH_2)_{16}$—C(O)—NH—$(CH_2)_{17}CH_3$) in various ratios, heating to 100° C., and mixing the molten mixture. The resulting compositions were allowed to cool and subsequently analyzed by DSC. The results are shown in Table 1, with the melting range determined from the peak width at ½ height.

TABLE 1

Thermal Analysis of Prior Art Compositions

| Stearone (wt %) | Octadecyl octadecamide (wt %) | Melting Point (° C.) | Melting Range (° C.) | Comment re DSC scan |
|---|---|---|---|---|
| 0 | 100 | 95 | 8 | Symmetrical |
| 30 | 70 | 85, 92 | 14 | Two peaks |
| 60 | 40 | 89 | 10 | Shallow onset |
| 70 | 30 | 86 | 13 | Shallow onset |
| 100 | 0 | 98 | 8 | Symmetrical |

The two pure compounds gave substantially narrower melting peaks and a significantly sharper onset, than any of the blends. It was also determined that the use of peak width at ⅓ height was a more relevant number for reporting temperature melting range than the traditionally reported peak width at ½ height.

Comparative Example 2

Figure 1B:
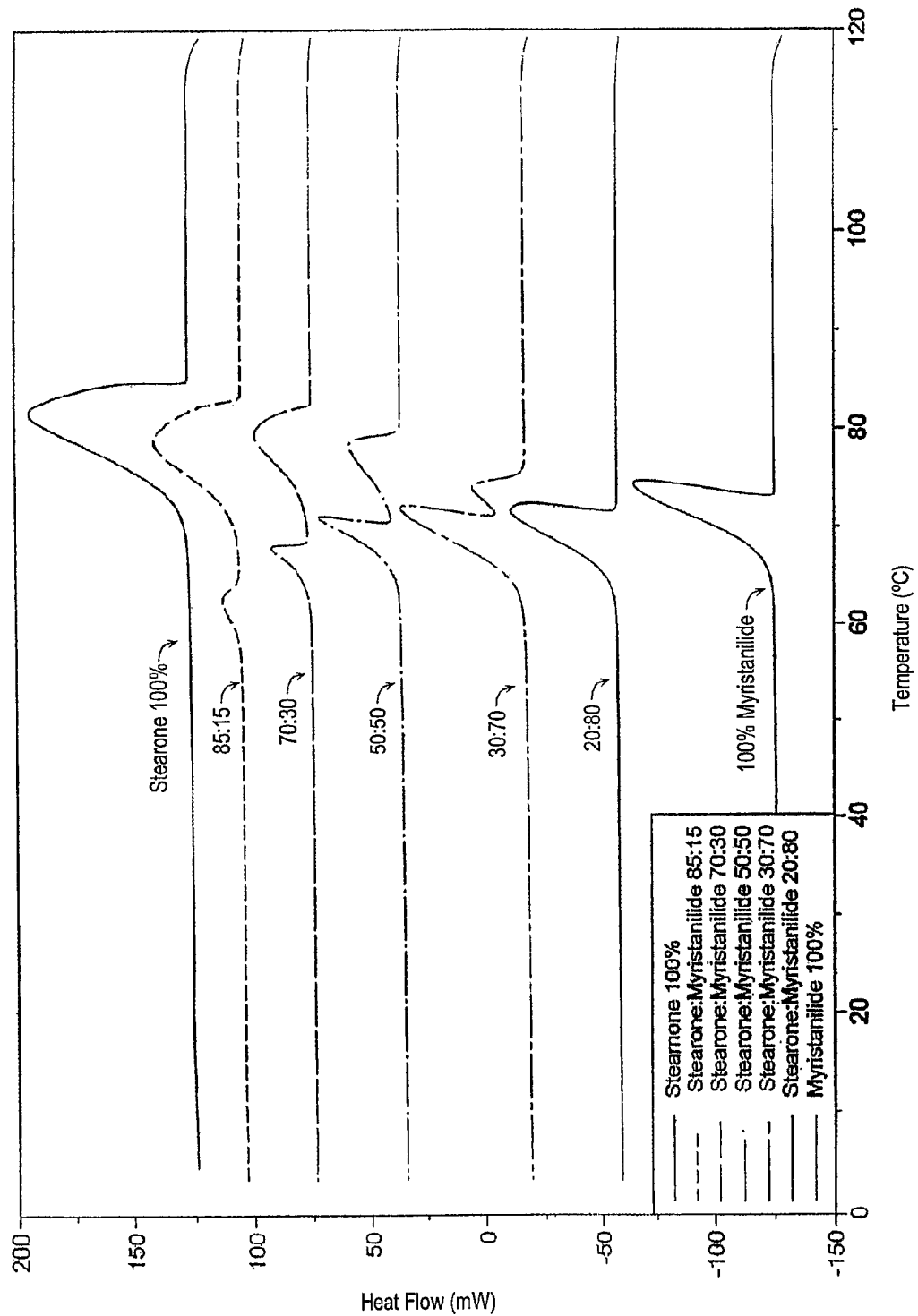

Organic eutectic mixtures as described in U.S. Pat. No. 5,537,950 were prepared by combining stearone (($C_{17}H_{35}$)—C(O)—($C_{17}H_{35}$)) and myristanalide (tetradecyl analide; $CH_3(CH_2)_{12}$—C(O)—NH—$C_6H_6$) in various ratios, heating to 100° C., and mixing the molten mixture. The resulting compositions were allowed to cool and subsequently analyzed by DSC. The results are shown in FIGS. 1A-1B and in Table 2.

TABLE 2

Thermal Analysis of Prior Art Compositions

| Stearone (wt %) | Myristanalide (wt %) | Melting Point (° C.) | Melting Range (° C.) | Comment re. DSC scan |
|---|---|---|---|---|
| 0 | 100 | 89 | 6 | Symmetrical |
| 20 | 80 | 84 | 6 | Onset slope |
| 30 | 70 | 84 | 6 | Onset slope |
| 50 | 50 | 82 | 8 | Double peak |
| 70 | 30 | 87 | 12 | Double peaks |
| 85 | 15 | 90 | 10 | Double peaks |
| 100 | 0 | 92 | 7 | Symmetrical |

Based on the DSC scans shown in FIGS. 1A-1B, it can be concluded based on the melting behavior that stearone and myristanalide are not sufficiently molecularly compatible to form a miscible polymer blend, as is apparent from the double peaks and onset slopes observed in the DSC scan. Also, small changes in compositional ratios resulted in large changes in the melting range. Only a small compositional range, e.g., 20:80 and 30:70 stearone:myristanalide, gives materials with acceptable melting characteristics. While not wishing to be bound by theory, it may be that the difference in chemical structure between stearone and myristanilide, one being an amide and the other being a ketone, makes them relatively incompatible for purposes of yielding a definite, sharp melting point and a narrow temperature melting range.

Example 1

Aliphatic Amide Compositions and Blends

A1. Synthesis of Aliphatic Amides

Aliphatic amides were prepared by combining equal molar amounts of aliphatic amine and aliphatic carboxylic acid in a two-neck flask equipped with a gas inlet tube and a short bath condenser and receiver attached to a vacuum trap and pump. The mixtures were heated from 160° C. to 210° C. for one hour and then vacuum was applied for an additional one hour to aid removal of water. Crude amide was then cooled and crystallized from ethanol until a constant melting point was obtained.

Melting transitions of the aliphatic amides were analyzed by DSC, according to the method given above. Trigger temperatures were evaluated using the method described above in the Definitions section. Results are shown in Tables 3A-3B and Table 4.

A2. Preparation of Blends of Aliphatic Amides

Blends of a first aliphatic amide and a second aliphatic amide were prepared by mixing the two materials in the desired ratio with heating above the melting point of the highest melting component.

In a first study, ten blends comprised of the following mixtures of symmetrical and unsymmetrical amides were prepared:

| Composition Identification No. | First Compound Name and Designation (wt %) | $^aR^1$ | $^aR^2$ | Second Compound Name and Designation (wt %) | $^bR_2^1$ | $^bR_2^2$ | $\|R^1-R_2^1\|$ $\|R^2-R_2^2\|$ |
|---|---|---|---|---|---|---|---|
| 1 (60:40 N-18-18/N-18-12) | n-octadecyl octadecamide N-18-18 (60) | $CH_3(CH_2)_{16}$ | $CH_3(CH_2)_{17}$ | n-octadecyl dodecamide N-18-12 (40) | $CH_3(CH_2)_{10}$ | $CH_3(CH_2)_{17}$ | 6 0 |
| 2 (5:95 N-18-18/N-18-12) | n-octadecyl octadecamide N-18-18 (5) | $CH_3(CH_2)_{16}$ | $CH_3(CH_2)_{17}$ | n-octadecyl dodecamide N-18-12 (95) | $CH_3(CH_2)_{10}$ | $CH_3(CH_2)_{17}$ | 6 0 |
| 3 (8:92 N-18-18/N-18-12) | n-octadecyl octadecamide N-18-18 (8) | $CH_3(CH_2)_{16}$ | $CH_3(CH_2)_{17}$ | n-dodecyl dodecamide N-12-12 (92) | $CH_3(CH_2)_{10}$ | $CH_3(CH_2)_{11}$ | 6 6 |
| 4 (10:90 N-18-18/N-18-8) | n-octadecyl octadecamide N-18-18 (10) | $CH_3(CH_2)_{16}$ | $CH_3(CH_2)_{17}$ | n-octadecyl octamide N-18-8 (90) | $CH_3(CH_2)_6$ | $CH_3(CH_2)_{17}$ | 10 0 |
| 5 (100% N-12-12) | n-hexadecyl hexadecamide N-16-16 (0) | $CH_3(CH_2)_{14}$ | $CH_3(CH_2)_{15}$ | n-dodecyl dodecamide N-12-12 (100) | $CH_3(CH_2)_{10}$ | $CH_3(CH_2)_{11}$ | — |
| 6 (30:70 N-16-16/N-12-12) | n-hexadecyl hexadecamide N-16-16 (30) | $CH_3(CH_2)_{14}$ | $CH_3(CH_2)_{15}$ | n-dodecyl dodecamide N-12-12 (70) | $CH_3(CH_2)_{10}$ | $CH_3(CH_2)_{11}$ | 4 4 |
| 7 (50:50 N-16-16/N-12-12) | n-hexadecyl hexadecamide N-16-16 (50) | $CH_3(CH_2)_{14}$ | $CH_3(CH_2)_{15}$ | n-dodecyl dodecamide N-12-12 (50) | $CH_3(CH_2)_{10}$ | $CH_3(CH_2)_{11}$ | 4 4 |
| 8 | n-hexadecyl hexadecamide | $CH_3(CH_2)_{14}$ | $CH_3(CH_2)_{15}$ | n-dodecyl dodecamide | $CH_3(CH_2)_{10}$ | $CH_3(CH_2)_{11}$ | |

-continued

| Composition Identification No. | First Compound Name and Designation (wt %) | $^a$R$^1$ | $^a$R$^2$ | Second Compound Name and Designation (wt %) | $^b$R$_2^1$ | $^b$R$_2^2$ | $\|R^1-R_2^1\|$ $\|R^2-R_2^2\|$ |
|---|---|---|---|---|---|---|---|
| (70:30 N-16-16/N-12-12) 9 | N-16-16 (70) n-hexadecyl hexadecamide | CH$_3$(CH$_2$)$_{14}$ | CH$_3$(CH$_2$)$_{15}$ | N-12-12 (30) n-dodecyl dodecamide | CH$_3$(CH$_2$)$_{10}$ | CH$_3$(CH$_2$)$_{11}$ | 4 — |
| (100 N-16-16) 10 | N-16-16 (100) 1,4 bis(oxyhexadecyl)piperazine | CH$_3$(CH$_2$)$_{14}$ | CH$_3$(CH$_2$)$_{14}$ | N-12-12 (0) 1,4 bis(oxytetradecyl)piperazine | CH$_3$(CH$_2$)$_{12}$ | CH$_3$(CH$_2$)$_{12}$ | 2 |
| (60:40 N-16-16-P/N-14-14-P) | N-16-16-P (60) | | | N-14-14-P (40) | | | 2 |

$^a$R$^1$—C(O)—NH—R$^2$
$^b$R$_2^1$—C(O)—NH—R$_2^2$

Blends 11-18 were characterized by DSC, according to the method given above. Trigger temperatures were evaluated using the method described above in the Definitions section. The results are shown in Table 5 and FIGS. 2A-2E.

In a second study, nine additional blends comprised of the symmetrical aliphatic amides n-hexadecyl hexadecamide and n-octadecyl octadecamide were prepared:

| Composition Identification No. | First Compound Name and Designation (wt %) | $^a$R$^1$ | $^a$R$^2$ | Second Compound Name and Designation (wt %) | $^b$R$_2^1$ | $^b$R$_2^2$ | $\|R^1-R_2^1\|$ $\|R^2-R_2^2\|$ |
|---|---|---|---|---|---|---|---|
| 11 (100% N-18-18) | n-octadecyl octadecamide N-18-18 (100) | CH$_3$(CH$_2$)$_{16}$ | CH$_3$(CH$_2$)$_{17}$ | n-hexadecyl hexadecamide N-16-16 (0) | CH$_3$(CH$_2$)$_{10}$ | CH$_3$(CH$_2$)$_{11}$ | 2 2 |
| 12 (80:20 N-18-18/N-16-16) | n-octadecyl octadecamide N-18-18 (80) | CH$_3$(CH$_2$)$_{16}$ | CH$_3$(CH$_2$)$_{17}$ | n-hexadecyl hexadecamide N-16-16 (20) | CH$_3$(CH$_2$)$_{10}$ | CH$_3$(CH$_2$)$_{11}$ | 2 2 |
| 13 (70:30 N-18-18/N-16-16) | n-octadecyl octadecamide N-18-18 (70) | CH$_3$(CH$_2$)$_{16}$ | CH$_3$(CH$_2$)$_{17}$ | n-hexadecyl hexadecamide N-16-16 (30) | CH$_3$(CH$_2$)$_{10}$ | CH$_3$(CH$_2$)$_{11}$ | 2 2 |
| 14 (50:50 N-18-18/N-16-16) | n-octadecyl octadecamide N-18-18 (60) | CH$_3$(CH$_2$)$_{16}$ | CH$_3$(CH$_2$)$_{17}$ | n-hexadecyl hexadecamide N-16-16 (40) | CH$_3$(CH$_2$)$_{10}$ | CH$_3$(CH$_2$)$_{11}$ | 2 2 |
| 15 (50:50 N-18-18/N-16-16) | n-octadecyl octadecamide N-18-18 (50) | CH$_3$(CH$_2$)$_{16}$ | CH$_3$(CH$_2$)$_{17}$ | n-hexadecyl hexadecamide N-16-16 (50) | CH$_3$(CH$_2$)$_{10}$ | CH$_3$(CH$_2$)$_{11}$ | 2 2 |
| 16 (40:60 N-18-18/N-16-16) | n-octadecyl octadecamide N-18-18 (40) | CH$_3$(CH$_2$)$_{16}$ | CH$_3$(CH$_2$)$_{17}$ | n-hexadecyl hexadecamide N-16-16 (60) | CH$_3$(CH$_2$)$_{10}$ | CH$_3$(CH$_2$)$_{11}$ | 2 2 |
| 17 (30:70 N-18-18/N-16-16) | n-octadecyl octadecamide N-18-18 (30) | CH$_3$(CH$_2$)$_{16}$ | CH$_3$(CH$_2$)$_{17}$ | n-hexadecyl hexadecamide N-16-16 (70) | CH$_3$(CH$_2$)$_{10}$ | CH$_3$(CH$_2$)$_{11}$ | 2 2 |
| 18 (20:80 N-18-18/N-16-16) | n-octadecyl octadecamide N-18-18 (20) | CH$_3$(CH$_2$)$_{16}$ | CH$_3$(CH$_2$)$_{17}$ | n-hexadecyl hexadecamide N-16-16 (80) | CH$_3$(CH$_2$)$_{10}$ | CH$_3$(CH$_2$)$_{11}$ | 2 2 |
| 19 (100% N-16-16) | n-octadecyl octadecamide N-18-18 (0) | CH$_3$(CH$_2$)$_{16}$ | CH$_3$(CH$_2$)$_{17}$ | n-hexadecyl hexadecamide N-16-16 (100) | CH$_3$(CH$_2$)$_{10}$ | CH$_3$(CH$_2$)$_{11}$ | 2 |

$^a$R$^1$—C(O)—NH—R$^2$
$^b$R$_2^1$—C(O)—NH—R$_2^2$

Blends 11-18 were characterized by DSC, according to the method given above, and the results are shown in Table 6 and FIG. 3.

Melting transitions of the benzamide blends were analyzed by DSC, according to the method given above. Trigger temperatures were evaluated using the method described above in the Definitions section. Results are shown in Tables 7A-7B and FIGS. 4A-4E.

Example 2

Benzamide Compositions and Blends

A1. Synthesis of Benzamides and Preparation of Blends

N-hexadecyl benzamide and n-octadecyl benzamide were prepared by condensing the n-alkyl amines (n-hexadecyl amine or n-octadecyl amine) with benzoic acid. The following blends were prepared by mixing the two component benzamides and heating:

Example 3

Linear N-Alkyl Anilide Compositions and Blends

A. Synthesis of N-alkyl Anilides and Preparation of Blends

A series of linear n-alkyl anilides were prepared by heating equamolar amounts of the alkyl carboxylic acid and analine at a temperature of from 160 to 220 C under reduced pressure for 6 hours. The resulting materials were recrystallized to constant melting points. Blends of the n-alkyl anilides were prepared by mixing the components in the desired ratios and heating. The following blends, nos. 30-32, were prepared. The compositions identified as 34 and 35 were prepared for comparison.

| Composition Identification No. | First Compound Name and Designation (wt %) | $^aR^1$ | $^aR^2$ | Second Compound Name and Designation (wt %) | $^bR_2^1$ | $^bR_2^2$ | $\|R^1-R_2^1\|$ $\|R^2-R_2^2\|$ |
|---|---|---|---|---|---|---|---|
| 20 (100% N-18-18) | n-octadecyl benzamide C18 BZA (100) | $C_6H_6$ | $CH_3(CH_2)_{17}$ | n-hexadecyl benzamide C16 BZA (0) | $C_6H_6$ | $CH_3(CH_2)_{15}$ | 0 2 |
| 21 (90:10 C18 BZA/C16 BZA) | n-octadecyl benzamide C18 BZA (90) | $C_6H_6$ | $CH_3(CH_2)_{17}$ | n-hexadecyl benzamide C16 BZA (10) | $C_6H_6$ | $CH_3(CH_2)_{15}$ | 0 2 |
| 22 (80:20 C18 BZA/C16 BZA) | n-octadecyl benzamide C18 BZA (80) | $C_6H_6$ | $CH_3(CH_2)_{17}$ | n-hexadecyl benzamide C16 BZA (20) | $C_6H_6$ | $CH_3(CH_2)_{15}$ | 0 2 |
| 23 (60:40 C18 BZA/C16 BZA) | n-octadecyl benzamide C18 BZA (60) | $C_6H_6$ | $CH_3(CH_2)_{17}$ | n-hexadecyl benzamide C16 BZA (40) | $C_6H_6$ | $CH_3(CH_2)_{15}$ | 0 2 |
| 24 (50:50 N-18-18/N-16-16) | n-octadecyl benzamide C18 BZA (50) | $C_6H_6$ | $CH_3(CH_2)_{17}$ | n-hexadecyl benzamide C16 BZA (50) | $C_6H_6$ | $CH_3(CH_2)_{15}$ | 0 2 |
| 25 (35:65 C18 BZA/C16 BZA) | n-octadecyl benzamide C18 BZA (35) | $C_6H_6$ | $CH_3(CH_2)_{17}$ | n-hexadecyl benzamide C16 BZA (65) | $C_6H_6$ | $CH_3(CH_2)_{15}$ | 0 2 |
| 26 (20:80 C18 BZA/C16 BZA) | n-octadecyl benzamide C18 BZA (20) | $C_6H_6$ | $CH_3(CH_2)_{17}$ | n-hexadecyl benzamide C16 BZA (80) | $C_6H_6$ | $CH_3(CH_2)_{15}$ | 0 2 |
| 27 (10:90 C18 BZA/C16 BZA) | n-octadecyl benzamide C18 BZA (10) | $C_6H_6$ | $CH_3(CH_2)_{17}$ | n-hexadecyl benzamide C16 BZA (90) | $C_6H_6$ | $CH_3(CH_2)_{15}$ | 0 2 |
| 28 (100% C16 BZA) | n-octadecyl benzamide C18 BZA (0) | $C_6H_6$ | $CH_3(CH_2)_{17}$ | n-hexadecyl benzamide C16 BZA (100) | $C_6H_6$ | $CH_3(CH_2)_{15}$ | 0 2 |

$^a R^1$—C(O)—NH—$R^2$
$^b R_2^1$—C(O)—NH—$R_2^2$

| Composition Identification No. | First Compound Name and Designation (wt %) | $^a R^1$ | $^a R^2$ | Second Compound Name and Designation (wt %) | $^b R_2^1$ | $^b R_2^2$ | $\|R^1-R_2^1\|$ $\|R^2-R_2^2\|$ |
|---|---|---|---|---|---|---|---|
| 29 | n-tetradecyl analide | $CH_3(CH_2)_{12}$ | $C_6H_6$ | n-dodecyl analide | $CH_3(CH_2)_{10}$ | $C_6H_6$ | 2 |
| (100% C14 ANA) | C14 ANA (100) | | | C12 ANA (0) | | | 0 |
| 30 | n-tetradecyl analide | $CH_3(CH_2)_{12}$ | $C_6H_6$ | n-dodecyl analide | $CH_3(CH_2)_{10}$ | $C_6H_6$ | 2 |
| (70:30 C14 ANA/C12 ANA) | C14 ANA (70) | | | C12 ANA (30) | | | 0 |
| 31 | n-tetradecyl analide | $CH_3(CH_2)_{12}$ | $C_6H_6$ | n-dodecyl analide | $CH_3(CH_2)_{10}$ | $C_6H_6$ | 2 |
| (50:50 C14 ANA/C12 ANA) | C14 ANA (50) | | | C12 ANA (50) | | | 0 |
| 32 | n-tetradecyl analide | $CH_3(CH_2)_{12}$ | $C_6H_6$ | n-dodecyl analide | $CH_3(CH_2)_{10}$ | $C_6H_6$ | 2 |
| (30:70 C14 ANA/C12 ANA) | C14 ANA (30) | | | C12 ANA (70) | | | 0 |
| 33 | n-tetradecyl analide | $CH_3(CH_2)_{12}$ | $C_6H_6$ | n-dodecyl analide | $CH_3(CH_2)_{10}$ | $C_6H_6$ | 2 |
| (100% C12 ANA) | C14 ANA (0) | | | C12 ANA (100) | | | 0 |
| 34 | n-tetradecyl analide | $CH_3(CH_2)_{12}$ | $C_6H_6$ | stearone$^c$ | $C_{17}H_{35}$ | $C_{17}H_{35}$ | 3 |
| (50:50 C14 ANA/stearone) | C14 ANA (50) | | | (50) | | | 11 |
| 35 | n-tetradecyl analide | $CH_3(CH_2)_{12}$ | $C_6H_6$ | n-octadecyl octadecamide | $CH_3(CH_2)_{16}$ | $CH_3(CH_2)_{17}$ | 4 |
| (50:50 C14 ANA/N-18-18) | C14 ANA (50) | | | N-18-18 (50) | | | 12 |

$^a R^1$—C(O)—NH—$R^2$
$^b R_2^1$—C(O)—NH—$R_2^2$
$^c (C_{17}H_{35})$—C(O)—$(C_{17}H_{35})$

The neat components and various blends of n-tetradecyl anilide and n-dodecyl anilide were characterized by DSC. The results are shown in Table 8.

Example 4

Temperature Indicating Device

C18 benzamide (90 wt %) and C16 benzamide (10 wt %) were mixed with warming in a container. The warm mixture was coated onto the center of a 2 cm×2 cm glass slide. A layer of epoxy was applied to the opposing side of the glass slide and a white paper with a 5 mm red circle was adhered to the epoxy, the red circle in alignment with the C18 BZA/C16 BZA coating in the center. The laminated device was allowed to dry. The mixture of 90 weight percent C18 BZA and 10 weight percent C16 BZA. The C18 BZA/C16 BZA coating was opaque after drying and the red circle was not visible.

The laminated device was heated to 85° C. and the red circle was visible as the overlying C18/BZA/C16 BZA mixture melted and became transparent.

Example 5

Reusable Temperature Indicating Component

A mixture of C18 BZA/C16 BZA (90:10 weight percent) was crystallized from hot methanol and collected as a fine white powder. One gram of the powder was mixed with 3 grams of a two-part epoxy resin to form an opaque white resin composite. The uncured resin was applied to a 2 cm×2 cm glass slide as a film of approximately 0.05 mm thick and allowed to cure at room temperature. After curing the film was opaque. The slide was heated to 85° C. and the film of resin became transparent. When cooled, the film became opaque.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A thermally-responsive device comprising a blend of two materials having a structure of:

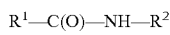

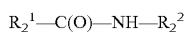

wherein each of $R^1$, $R^2$, $R_2^1$, and $R_2^2$ is independently a saturated alkyl having between 7-22 carbon atoms, wherein the number of carbon atoms in $R^1$ and $R^2$ differs by an absolute value of four or less; and wherein the number of carbon atoms in $R_2^2$ differs from the number of carbon atoms in $R^2$ by an absolute value of four or less, and wherein said device has a trigger temperature that occurs over a temperature range of less than about 2° C.

2. The device according to claim 1, wherein $R^1$ is a saturated alkyl having between 7-21 carbon atoms and $R^2$ is a saturated alkyl having between 8-22 carbon atoms, wherein the number of carbon atoms in $R^2$ differs from the number of carbon atoms in $R^1$ by an absolute value of zero, one, two, or three.

3. The device according to claim 1, wherein $R^1$ is $CH_3(CH_2)_{10}$ and $R^2$ is $CH_3(CH_2)_{11}$.

4. The device according to claim 1, wherein $R^1$ is $CH_3(CH_2)_8$ and $R^2$ is $CH_3(CH_2)_{11}$.

5. The device according to claim 1, wherein $R^1$ is $CH_3(CH_2)_{16}$ and $R^2$ is $CH_3(CH_2)_{17}$.

6. The device according to claim 1, wherein $R^1$ is $CH_3(CH_2)_{14}$ and $R^2$ is $CH_3(CH_2)_{15}$.

7. The device according to claim 1, wherein $R^1$ is $CH_3(CH_2)_{20}$ and $R^2$ is $CH_3(CH_2)_{17}$.

8. The device according to claim 1, wherein each of $R^1$ and $R_2^1$ are independently a saturated alkyl having between 9-19 carbon atoms, and each of $R^2$ and $R_2^2$ independently ndependently a saturated alkyl having between 10-20 carbon atoms, wherein the number of carbon atoms in $R^1$ or $R^2$ differs from the number of carbon atoms in $R_2^1$ or $R_2^2$, respectively, by one, two, three, or four.

9. The device according to claim 1, wherein $R^1$ and $R_2^1$ are independently a saturated alkyl having between 9-19 carbon atoms, and each of $R^2$ and $R_2^2$ are independently a saturated alkyl having between 10-20 carbon atoms, wherein the number of carbon atoms in $R^2$ is greater than the number of carbon atoms in $R_2^2$ by two or four.

10. The device according to claim 1, wherein $R^1$ is $CH_3(CH_2)_{10}$ and $R^2$ is $CH_3(CH_2)_{11}$ and wherein $R_2^1$ is $CH_3(CH_2)_{14}$ and $R_2^2$ is $CH_3(CH_2)_{15}$.

11. The device according to claim 1, wherein $R^1$ is $CH_3(CH_2)_{16}$ and $R^2$ is $CH_3(CH_2)_{17}$ and wherein $R_2^1$ is $CH_3(CH_2)_{12}$ and $R_2^2$ is $CH_3(CH_2)_{13}$.

12. The device according to claim 1, wherein $R^1$ is $CH_3(CH_2)_{14}$ and $R^2$ is $CH_3(CH_2)_{15}$ and wherein $R_2^1$ is $CH_3(CH_2)_{12}$ and $R_2^2$ is $CH_3(CH_2)_{13}$.

13. The device according to claim 1, wherein $R^1$ is $CH_3(CH_2)_{16}$ and $R^2$ is $CH_3(CH_2)_{17}$ and wherein $R_2^1$ is $CH_3(CH_2)_{14}$ and $R_2^2$ is $CH_3(CH_2)_{15}$.

14. The device according to claim 1, wherein $R^1$ is $CH_3(CH_2)_{16}$ and $R^2$ is $CH_3(CH_2)_{17}$ and wherein $R_2^1$ is $CH_3(CH_2)_{20}$ and $R_2^2$ is $CH_3(CH_2)_{21}$.

15. The device according to claim 1, wherein the trigger temperature is between 70-100° C.

* * * * *